United States Patent
Gorczynski

(10) Patent No.: US 7,205,386 B2
(45) Date of Patent: Apr. 17, 2007

(54) TRUNCATED CD200

(75) Inventor: Reginald M. Gorczynski, Willowdale (CA)

(73) Assignee: Trillium Therapeutics Inc., Toronto, Ontario (CA)

( * ) Notice: Subject to any disclaimer, the term of this patent is extended or adjusted under 35 U.S.C. 154(b) by 378 days.

(21) Appl. No.: 10/416,510

(22) PCT Filed: Nov. 22, 2001

(86) PCT No.: PCT/CA01/01641

§ 371 (c)(1),
(2), (4) Date: Oct. 8, 2003

(87) PCT Pub. No.: WO02/42332

PCT Pub. Date: May 30, 2002

(65) Prior Publication Data

US 2004/0054145 A1    Mar. 18, 2004

Related U.S. Application Data

(60) Provisional application No. 60/252,424, filed on Nov. 22, 2000.

(51) Int. Cl.
*C07K 14/435* (2006.01)
*C07K 14/705* (2006.01)

(52) U.S. Cl. .................................... 530/350

(58) Field of Classification Search .................... None
See application file for complete search history.

(56) References Cited

U.S. PATENT DOCUMENTS 6,338,851 B1 *  1/2002  Gorczynski ............. 424/185.1

FOREIGN PATENT DOCUMENTS

| WO | WO 99/24565 | 5/1999 |
| WO | WO 02/11762 | 2/2002 |

OTHER PUBLICATIONS

Burgess et al. J Cell Biol. 111:2129-2138, 1990.*
Lazar et al., Mol Cell Biol. 8:1247-1252, 1988.*
Metzler et al., Nature Structural Biol. 1997; 4:527-531.*
Bowie et al., Science, 247:1306-1310, 1990.*
Attwood, Science 2000; 290:471-473.*
Skolnick et al., Trends in Biotech. 2000; 18(1):34-39.*
Borriello et al., Mammalian Genome, 1998, 9: 114-118.*
Cseke et al., Handbook of Molecular and Cellular Methods in Biology and Medicine, CRC Press, 2004, p. 96.*
Gorczynski, Reginald M. et al., "An Immunoadhesin Incorporating the Molecule OX-2 Is a Potent Immunosuppressant That Prolongs Allo- and Xenograft Survival", Journal of Immunology (Baltimore, MD: 1950) United States Aug. 1, 1999, vol. 163, No. 3, pp. 1654-1660.
Gorczynski, Reginald M. et al., "Anti-Rat OX-2 Blocks Increased Small Intestinal Transplant Survival After Portal Vein Imunization", Transplantation Proceedings, vol. 31, No. 1-2, Feb. 1999 pp. 577-578, XP002222033 XVIIth World Congress of the Transplantation Society; Jul. 12-17, 1998.
Takeda, J. "Similar to OX-2 cell Surface Antigen", Database EMBL 'Online!, Feb. 9, 1996, Database accession No. D82639, XP002222034, The sequence.
Lee, N. H. et al., "EST291980 Normalized rat ovary, Bento Soares Rattus sp. cDNA clone RGICL47 5' end similar to cell surface protein MRC OX-2, mRNA sequence", Database EMBL 'Online!, Nov. 2, 1999, Database accession No. AW141865 XP002222035, The sequence.
Konno, H. et al., "Mus musculus 10 days neonate cortex cDNA, RIKEN full-length enriched library, clone:A830086N06, 3' end partial sequence, similar to ddbj:AF004023 Mus musculus cell surface molecule OX-2 mRNA", Database 'Online!, Jul. 2, 2000, Database accession No. BB274162, XP002222036, The sequence.
Steurer, W. et al., "Ex Vivo Coating of Islet Cell Allografts With Murine CLTA4/FC Promotes Graft Tolerance", Journal of Immunology The Williams and Wilkins Co., Baltimore, U.S., vol. 155, No. 3, Aug. 1, 1995, pp. 1165-1174, XP002031135.

* cited by examiner

*Primary Examiner*—Phillip Gambel
*Assistant Examiner*—Ilia Ouspenski
(74) *Attorney, Agent, or Firm*—Bereskin & Parr; Micheline Gravelle

(57) ABSTRACT

A truncated form of the full-length, immunosuppression-inducing molecule, CD200, $CD200_{tr}$, was expressed in CHO cells and the transduced cells used to produce mAbs to $CD200_{tr}$. These mAbs detect simultaneous expression of full-length CD200 and $CD200_{tr}$ in LPS-stimulated dendritic cells (DCs). Moreover, CHO cells and DCs expressing $CD200_{tr}$ as well as soluble $CD200_{tr}$ are able to inhibit suppression of mixed leucocyte reactions in vitro which follows addition of the soluble form of CD200 (CD200:Fc) in culture, demonstrating that $CD200_{tr}$ is a physiological antagonist of CD200.

6 Claims, 9 Drawing Sheets

```
                                   Leader ----------
                    GTGATCAGGATGCCCTTCTCTCATCTCTCCTCCTACAGCCTGGTTTGGGTCATGG     55
                          |V-like domain -----------
CAGCAGTGGTGCTGTGCACAGCACAAGTGCAAGTGGTGACCCAGGATGAAAGAAAGGAGCTGTACAC            122
AACTGCTTCCTTAAAATCTTCTCGCAAAAATGCCCAGGAACGCTCGCTTGTGACATGGCAGAAAAG             189
AAAGCTGTGAGCCCAGAAAACATGGTCACCTTCAGCGAGAACCATGGGGTGGTGATCCAGCCTGCCT            256
ATAAGGACAAGATAAATGTTACCCAGCTGGGACTCCGAAACTCAACCATCACCTTCTGGAATATCCA            323
CATTGGGGATGGAGGGTGTTACATGTGTCTCTTCAATACCTTTGGTTTTCAGAAGGTCTCAGGAACA            390
                           |C-like domain ----------
GCCTGCCTCACCGTCTATGTACAGCCCATAGTATCCCTTCACTACAAATTCTCTGAACACCACCTAA            457
ATATCACTTGCTCTGCCACTGCCCGTCCAGCCCCCATGGTCATCTGGAAGGTTCCCGGGACAGGAAT            524
TGAAAATAGTACAGTGACTCTGTTTCACCCAAATGGGACCACGTCTGTTACCAGCATCCTCCATATC            591
AAAGACCCTAAGAATCAGGTGGGGAAGGAAGTGATCTGCCAGGTGCTGCACCTGGGGACTGTGACCG            658
                          |Transmembrane region ---------
ACTTTAAGCAAACCGTCAACAAAGGCTATTGGTTTTCAGTTCCGCTATTGCTAAGCATTGTTTCCCT            725
                                |Cytoplasmic region ---------
GGTAATTCTTCTCATCCTAATCTCAATCTTACTGTACTGGAAACGTCACCGGAATCAGGACCGAGGT            792
GAATTGTCACAGGGAGTTCAAAAAATGACATAA                                              825
```

Human CD200 and CD200$_{tr}$: Alternate translational start site for CD200$_{tr}$ shown in bold/italic. This leads to complete CD200$_{tr}$ sequence below:

B

```
Start: Truncated V-region-domain------
ATGGTCACCTTCAGCGAGAACCATGGGGTGGTGATCCAGCCTGCCTATAAGGACAAGATAAATGTTA      67
CCCAGCTGGGACTCCGAAACTCAACCATCACCTTCTGGAATATCCACATTGGGGATGGAGGGTGTTA      134
CATGTGTCTCTTCAATACCTTTGGTTTTCAGAAGGTCTCAGGAACAGCCTGCCTCACCGTCTATGTA      201
|C-like domain ---------
CAGCCCATAGTATCCCTTCACTACAAATTCTCTGAACACCACCTAAATATCACTTGCTCTGCCACTG      268
CCCGTCCAGCCCCCATGGTCATCTGGAAGGTTCCCGGGACAGGAATTGAAAATAGTACAGTGACTCT      335
GTTTCACCCAAATGGGACCACGTCTGTTACCAGCATCCTCCATATCAAAGACCCTAAGAATCAGGTG      402
GGGAAGGAAGTGATCTGCCAGGTGCTGCACCTGGGGACTGTGACCGACTTTAAGCAAACCGTCAACA      469
      |Transmembrane region ----------
AAGGCTATTGGTTTTCAGTTCCGCTATTGCTAAGCATTGTTTCCCTGGTAATTCTTCTCATCCTAAT      536
             |Cytoplasmic region ---------
CTCAATCTTACTGTACTGGAAACGTCACCGGAATCAGGACCGAGGTGAATTGTCACAGGGAGTTCAA      603
AAAATGACATAA                                                             615
```

Leader sequence (CD200)----------
ATGGGCAGTCTGGTATTCAGGAGACCTTTCTGCCATCTCTCCACCTACAGCCTGATTTGGGGCATAG   67
                |V-like domain -----------
CAGCAGTAGCGCTGAGCACAGCTCAAGTGGAAGTGGTGACCCAGGATGAAAGAAAGGCGCTGCACAC   134
AACTGCATCCTTACGATGTTCTCTAAAAACATCCCAGGAACCCTTGATTGTGACATGGCAGAAAAAG   201
AAAGCCGTGAGCCCAGAAAAC*ATGGTCACCTACAGCAAAACCCATGGGGTTGTAATCCAGCCTGCCT*   268
ACAAAGACAGGATAAATGTCACAGAGCTGGGACTCTGGAACTCAAGCATCACCTTCTGGAACACACA   335
CATTGGAGATGGAGGCTGCTACATGTGTCTCTTCAACACGTTTGGTTCTCAGAAGGTCTCAGGAACA   402
              |C-like domain ---------
GCTTGCCTTACTCTCTATGTACAGCCCATAGTACACCTTCACTACAACTATTTTGAACACCACCTAA   469
ACATCACTTGCTCTGCGACTGCCCGTCCAGCCCCTGCCATCACCTGGAAGGGTACTGGGACAGGAAT   536
TGAGAATAGTACCGAGAGTCACTTCCATTCAAATGGGACTACATCTGTCACCAGCATCCTCCGGGTC   603
AAAGACCCCAAAACTCAGGTTGGAAAGGAAGTGATCTGCCAGGTTTTATACTTGGGGAATGTGATTG   670
                  |Transmembrane region ---------
ACTACAAGCAGAGTCTGGACAAAGGATTTTGGTTTTCAGTTCCACTGTTGCTAAGCATTGTTTCTCT   737
                        |Cytoplasmic region ----------
GGTAATTCTTCTGATCTTGATCTCCATCTTACTATACTGGAAACGTCACCGAAATCAGGAGCGGGGT   804
GAATCATCACAGGGGATGCAAAGAATGAAATAA   837

Mouse CD200 and CD200$_{tr}$: beginning of renewed transcription following
alternate splicing shown in italics (bold).... This leads to CD200$_{tr}$ cDNA
sequence below:

B

Start: truncated V-region-domain
ATGGTCACCTACAGCAAAACCCATGGGGTTGTAATCCAGCCTGCCTACAAAGACAGGATAAATGTCA   67
CAGAGCTGGGACTCTGGAACTCAAGCATCACCTTCTGGAACACACACATTGGAGATGGAGGCTGCTA   134
CATGTGTCTCTTCAACACGTTTGGTTCTCAGAAGGTCTCAGGAACAGCTTGCCTTACTCTCTATGTA   201
|C-like domain ---------
CAGCCCATAGTACACCTTCACTACAACTATTTTGAACACCACCTAAACATCACTTGCTCTGCGACTG   268
CCCGTCCAGCCCCTGCCATCACCTGGAAGGGTACTGGGACAGGAATTGAGAATAGTACCGAGAGTCA   335
CTTCCATTCAAATGGGACTACATCTGTCACCAGCATCCTCCGGGTCAAAGACCCCAAAACTCAGGTT   402
GGAAAGGAAGTGATCTGCCAGGTTTTATACTTGGGGAATGTGATTGACTACAAGCAGAGTCTGGACA   469
       |Transmembrane region ---------
AAGGATTTTGGTTTTCAGTTCCACTGTTGCTAAGCATTGTTTCTCTGGTAATTCTTCTGATCTTGAT   536
             |Cytoplasmic region ---------
CTCCATCTTACTATACTGGAAACGTCACCGAAATCAGGAGCGGGGTGAATCATCACAGGGGATGCAA   603
AGAATGAAATAA   615

FIGURE 3

Comparison of the protein sequence of human MRC CD200 and CD200$_{tr}$

A

Human CD200

|V-like domain (domain I) ————————                *
HUM    Q V Q V V T Q D E R E L L Y T T A S L K C S L Q N A Q E A L

HUM    I V T W Q K K K A V G P E N M V T Y S E N H G V V I Q P T Y

HUM    K D K I N I T Q L G L Q N T T I T F W N I T L E D G G C Y M
         *                                          | C-like domain (domain II)—
HUM    C L F N M F G F G K V S G T A C V T L Y V Q P I V S L H Y K
                               *
HUM    F S E H H L N I T C S A T A R P A P M V F W K V P R S G I E HUM    N S T V T L S H P N G T T S V T S I L H I K D P K N Q V G K
            *                                          |Transmembrane region —
HUM    E V I C Q V L H L G T V T D F K Q T V N K G Y W F S V P L L
                                                       | Cytoplasmic region ————
HUM    L S I V S L V I L L V L I S I L L Y W K R H R N Q D R G E L

HUM    S Q G V Q K M T

B

Human CD200$_{tr}$

Modified V-like domain (domain I) ————————
HUM    E N M V T Y S E N H G V V I Q P T Y K D K I N I T Q L G L Q
                                 *
HUM    N T T I T F W N I T L E D G G C Y M C L F N M F G F G K V S
                            | C-like domain (domain II)—              *
HUM    G T A C V T L Y V Q P I V S L H Y K F S E H H L N I T C S A HUM    T A R P A P M V F W K V P R S G I E N S T V T L S H P N G T
                                                    *
HUM    T S V T S I L H I K D P K N Q V G K E V I C Q V L H L G T V
                                  |Transmembrane region —
HUM    T D F K Q T V N K G Y W F S V P L L L S I V S L V I L L V L I
                            | Cytoplasmic region ————
HUM    S I L L Y W K R H R N Q D R G E L S Q G V Q K M T Note: * denotes invariant cysteine residues (across species)

FIGURE 4

Comparison of the protein sequence of mouse CD200 and CD200$_{tr}$

A

|V-like domain (domain I) ———                                        *

CD200   Q V E V V T Q D E R K A L H T T A S L R C S L K T S Q E P L

I V T W Q K K K A V S P E N M V T Y S K T H G V V I Q P A Y

K D R I N V T E L G L W N S S I T F W N T H I G D G G C Y M

*                                       | C-like domain (domain II)--
C L F N T F G S Q K V S G T A C L T L Y V Q P I V H L H Y N
                      *

Y F E H H L N I T C S A T A R P A P A I T W K G T G T G I E

N S T E S H F H S N G T T S V T S I L R V K D P K T Q V G K

*                                        |Transmembrane region --
E V I C Q V L Y L G N V I D Y K Q S L D K G F W F S V P L L

| Cytoplasmic region ——————
L S I V S L V I L L I L I S I L L Y W K R H R N Q E R G E S

S Q G M Q R M K

B

CD200$_{tr}$ Modified V-region domain........
        E N M V T Y S K T H G V V I Q P A Y K D R I N V T E L G L W
                              *
        N S S I T F W N T H I G D G G C Y M C L F N T F G S Q K V S

| C-like domain (domain II)--           *
        G T A C L T L Y V Q P I V H L H Y N Y F E H H L N I T C S A T A R P A P A I T W K G T G T G I E N S T E S H F H S N G T
                                                *
        T S V T S I L R V K D P K T Q V G K E V I C Q V L Y L G N V

|Transmembrane region --
        I D Y K Q S L D K G F W F S V P L L L S I V S L V I L L I L I

| Cytoplasmic region ——————
        S I L L Y W K R H R N Q E R G E S S Q G M Q R M K

*Note:* * delineates invariant cysteines in CD200 framework (across species)

CD200tr is a competitive antagonist of inhibition resulting from addition of CD200Fc in culture

SEQUENCE LISTING

<160> NUMBER OF SEQ ID NOS: 10

<210> SEQ ID NO 1
<211> LENGTH: 825
<212> TYPE: DNA
<213> ORGANISM: Homo sapiens

<400> SEQUENCE: 1

```
gtgatcagga tgcccttctc tcatctctcc tcctacagcc tggtttgggt catggcagca      60
gtggtgctgt gcacagcaca agtgcaagtg gtgacccagg atgaaagaaa ggagctgtac     120
acaactgctt ccttaaaatc ttctcgcaaa aatgcccagg aacgctcgct tgtgacatgg     180
cagaaaaaga aagctgtgag cccagaaaac atggtcacct tcagcgagaa ccatggggtg     240
gtgatccagc ctgcctataa ggacaagata aatgttaccc agctgggact ccgaaactca     300
accatcacct tctggaatat ccacattggg gatggagggt gttacatgtg tctcttcaat     360
acctttggtt ttcagaaggt ctcaggaaca gcctgcctca ccgtctatgt acagcccata     420
gtatcccttc actacaaatt ctctgaacac cacctaaata tcacttgctc tgccactgcc     480
cgtccagccc ccatggtcat ctggaaggtt cccgggacag gaattgaaaa tagtacagtg     540
actctgtttc acccaaatgg gaccacgtct gttaccagca tcctccatat caaagaccct     600
aagaatcagg tggggaagga agtgatctgc caggtgctgc acctggggac tgtgaccgac     660
tttaagcaaa ccgtcaacaa aggctattgg ttttcagttc cgctattgct aagcattgtt     720
tccctggtaa ttcttctcat cctaatctca atcttactgt actggaaacg tcaccggaat     780
caggaccgag gtgaattgtc acagggagtt caaaaaatga cataa                    825
```

<210> SEQ ID NO 2
<211> LENGTH: 615
<212> TYPE: DNA
<213> ORGANISM: Homo sapiens

<400> SEQUENCE: 2

```
atggtcacct tcagcgagaa ccatggggtg gtgatccagc ctgcctataa ggacaagata      60
```

-continued

| | |
|---|---|
| aatgttaccc agctgggact ccgaaactca accatcacct tctggaatat ccacattggg | 120 |
| gatggagggt gttacatgtg tctcttcaat acctttggtt ttcagaaggt ctcaggaaca | 180 |
| gcctgcctca ccgtctatgt acagcccata gtatcccttc actacaaatt ctctgaacac | 240 |
| cacctaaata tcacttgctc tgccactgcc cgtccagccc ccatggtcat ctggaaggtt | 300 |
| cccgggacag gaattgaaaa tagtacagtg actctgtttc acccaaatgg gaccacgtct | 360 |
| gttaccagca tcctccatat caaagaccct aagaatcagg tggggaagga agtgatctgc | 420 |
| caggtgctgc acctggggac tgtgaccgac tttaagcaaa ccgtcaacaa aggctattgg | 480 |
| ttttcagttc cgctattgct aagcattgtt tccctggtaa ttcttctcat cctaatctca | 540 |
| atcttactgt actggaaacg tcaccggaat caggaccgag gtgaattgtc acagggagtt | 600 |
| caaaaaatga cataa | 615 |

<210> SEQ ID NO 3
<211> LENGTH: 837
<212> TYPE: DNA
<213> ORGANISM: Murine

<400> SEQUENCE: 3

| | |
|---|---|
| atgggcagtc tggtattcag gagacctttc tgccatctct ccacctacag cctgatttgg | 60 |
| ggcatagcag cagtagcgct gagcacagct caagtggaag tggtgaccca ggatgaaaga | 120 |
| aaggcgctgc acacaactgc atccttacga tgttctctaa aacatcccca ggaaccttg | 180 |
| attgtgacat ggcagaaaaa gaaagccgtg agcccagaaa acatggtcac ctacagcaaa | 240 |
| acccatgggg ttgtaatcca gcctgcctac aaagacagga taaatgtcac agagctggga | 300 |
| ctctggaact caagcatcac cttctggaac acacacattg gagatggagg ctgctacatg | 360 |
| tgtctcttca acacgtttgg ttctcagaag gtctcaggaa cagcttgcct tactctctat | 420 |
| gtacagccca gtacacctt tcactacaac tattttgaac accacctaaa catcacttgc | 480 |
| tctgcgactg cccgtccagc ccctgccatc acctggaagg gtactgggac aggaattgag | 540 |
| aatagtaccg agagtcactt ccattcaaat gggactacat ctgtcaccag catcctccgg | 600 |
| gtcaaagacc ccaaaactca ggttggaaag gaagtgatct gccaggtttt atacttgggg | 660 |
| aatgtgattg actacaagca gagtctggac aaaggatttt ggtttttcagt tccactgttg | 720 |
| ctaagcattg tttctctggt aattcttctg atcttgatct ccatcttact atactggaaa | 780 |
| cgtcaccgaa tcaggagcg ggtgaatca tcacagggga tgcaaagaat gaaataa | 837 |

<210> SEQ ID NO 4
<211> LENGTH: 615
<212> TYPE: DNA
<213> ORGANISM: Murine

<400> SEQUENCE: 4

| | |
|---|---|
| atggtcacct acagcaaaac ccatggggtt gtaatccagc ctgcctacaa agacaggata | 60 |
| aatgtcacag agctgggact ctggaactca agcatcacct tctggaacac acacattgga | 120 |
| gatggaggct gctacatgtg tctcttcaac acgtttggtt ctcagaaggt ctcaggaaca | 180 |
| gcttgcctta ctctctatgt acagcccata gtacaccttc actacaacta ttttgaacac | 240 |
| cacctaaaca tcacttgctc tgcgactgcc cgtccagccc ctgccatcac ctggaaggggt | 300 |
| actgggacag gaattgagaa tagtaccgag agtcacttcc attcaaatgg gactacatct | 360 |
| gtcaccagca tcctccgggt caaagacccc aaaactcagg ttggaaagga agtgatctgc | 420 |
| caggttttat acttggggaa tgtgattgac tacaagcaga gtctggacaa aggattttgg | 480 |

```
ttttcagttc cactgttgct aagcattgtt tctctggtaa ttcttctgat cttgatctcc    540
atcttactat actggaaacg tcaccgaaat caggagcggg gtgaatcatc acagggatg     600 caaagaatga aataa                                                    615
```

<210> SEQ ID NO 5
<211> LENGTH: 248
<212> TYPE: PRT
<213> ORGANISM: Homo sapiens

<400> SEQUENCE: 5

```
Gln Val Gln Val Val Thr Gln Asp Glu Arg Glu Leu Leu Tyr Thr Thr
1               5                   10                  15

Ala Ser Leu Lys Cys Ser Leu Gln Asn Ala Gln Glu Ala Leu Ile Val
            20                  25                  30

Thr Trp Gln Lys Lys Lys Ala Val Gly Pro Glu Asn Met Val Thr Tyr
        35                  40                  45

Ser Glu Asn His Gly Val Val Ile Gln Pro Thr Tyr Lys Asp Lys Ile
    50                  55                  60

Asn Ile Thr Gln Leu Gly Leu Gln Asn Thr Thr Ile Thr Phe Trp Asn
65                  70                  75                  80

Ile Thr Leu Glu Asp Gly Gly Cys Tyr Met Cys Leu Phe Asn Met Phe
                85                  90                  95

Gly Phe Gly Lys Val Ser Gly Thr Ala Cys Val Thr Leu Tyr Val Gln
            100                 105                 110

Pro Ile Val Ser Leu His Tyr Lys Phe Ser Glu His His Leu Asn Ile
        115                 120                 125

Thr Cys Ser Ala Thr Ala Arg Pro Ala Pro Met Val Phe Trp Lys Val
    130                 135                 140

Pro Arg Ser Gly Ile Glu Asn Ser Thr Val Thr Leu Ser His Pro Asn
145                 150                 155                 160

Gly Thr Thr Ser Val Thr Ser Ile Leu His Ile Lys Asp Pro Lys Asn
                165                 170                 175

Gln Val Gly Lys Glu Val Ile Cys Gln Val Leu His Leu Gly Thr Val
            180                 185                 190

Thr Asp Phe Lys Gln Thr Val Asn Lys Gly Tyr Trp Phe Ser Val Pro
        195                 200                 205

Leu Leu Leu Ser Ile Val Ser Leu Val Ile Leu Val Leu Ile Ser
    210                 215                 220

Ile Leu Leu Tyr Trp Lys Arg His Arg Asn Gln Asp Arg Gly Glu Leu
225                 230                 235                 240

Ser Gln Gly Val Gln Lys Met Thr
                245
```

<210> SEQ ID NO 6
<211> LENGTH: 206
<212> TYPE: PRT
<213> ORGANISM: Homo sapiens

<400> SEQUENCE: 6

```
Glu Asn Met Val Thr Tyr Ser Glu Asn His Gly Val Val Ile Gln Pro
1               5                   10                  15

Thr Tyr Lys Asp Lys Ile Asn Ile Thr Gln Leu Gly Leu Gln Asn Thr
            20                  25                  30

Thr Ile Thr Phe Trp Asn Ile Thr Leu Glu Asp Gly Gly Cys Tyr Met
        35                  40                  45
```

```
Cys Leu Phe Asn Met Phe Gly Phe Gly Lys Val Ser Gly Thr Ala Cys
 50                  55                  60

Val Thr Leu Tyr Val Gln Pro Ile Val Ser Leu His Tyr Lys Phe Ser
 65                  70                  75                  80

Glu His His Leu Asn Ile Thr Cys Ser Ala Thr Ala Arg Pro Ala Pro
                 85                  90                  95

Met Val Phe Trp Lys Val Pro Arg Ser Gly Ile Glu Asn Ser Thr Val
            100                 105                 110

Thr Leu Ser His Pro Asn Gly Thr Thr Ser Val Thr Ser Ile Leu His
            115                 120                 125

Ile Lys Asp Pro Lys Asn Gln Val Gly Lys Glu Val Ile Cys Gln Val
130                 135                 140

Leu His Leu Gly Thr Val Thr Asp Phe Lys Gln Thr Val Asn Lys Gly
145                 150                 155                 160

Tyr Trp Phe Ser Val Pro Leu Leu Leu Ser Ile Val Ser Leu Val Ile
                165                 170                 175

Leu Leu Val Leu Ile Ser Ile Leu Leu Tyr Trp Lys Arg His Arg Asn
            180                 185                 190

Gln Asp Arg Gly Glu Leu Ser Gln Gly Val Gln Lys Met Thr
            195                 200                 205

<210> SEQ ID NO 7
<211> LENGTH: 248
<212> TYPE: PRT
<213> ORGANISM: Murine

<400> SEQUENCE: 7

Gln Val Glu Val Val Thr Gln Asp Glu Arg Lys Ala Leu His Thr Thr
 1               5                  10                  15

Ala Ser Leu Arg Cys Ser Leu Lys Thr Ser Gln Glu Pro Leu Ile Val
                20                  25                  30

Thr Trp Gln Lys Lys Lys Ala Val Ser Pro Glu Asn Met Val Thr Tyr
             35                  40                  45

Ser Lys Thr His Gly Val Val Ile Gln Pro Ala Tyr Lys Asp Arg Ile
 50                  55                  60

Asn Val Thr Glu Leu Gly Leu Trp Asn Ser Ser Ile Thr Phe Trp Asn
 65                  70                  75                  80

Thr His Ile Gly Asp Gly Gly Cys Tyr Met Cys Leu Phe Asn Thr Phe
                 85                  90                  95

Gly Ser Gln Lys Val Ser Gly Thr Ala Cys Leu Thr Leu Tyr Val Gln
            100                 105                 110

Pro Ile Val His Leu His Tyr Asn Tyr Phe Glu His His Leu Asn Ile
            115                 120                 125

Thr Cys Ser Ala Thr Ala Arg Pro Ala Pro Ala Ile Thr Trp Lys Gly
130                 135                 140

Thr Gly Thr Gly Ile Glu Asn Ser Thr Glu Ser His Phe His Ser Asn
145                 150                 155                 160

Gly Thr Thr Ser Val Thr Ser Ile Leu Arg Val Lys Asp Pro Lys Thr
                165                 170                 175

Gln Val Gly Lys Glu Val Ile Cys Gln Val Leu Tyr Leu Gly Asn Val
            180                 185                 190

Ile Asp Tyr Lys Gln Ser Leu Asp Lys Gly Phe Trp Phe Ser Val Pro
            195                 200                 205

Leu Leu Leu Ser Ile Val Ser Leu Val Ile Leu Leu Ile Leu Ile Ser
```

```
                210             215             220
Ile Leu Leu Tyr Trp Lys Arg His Arg Asn Gln Glu Arg Gly Glu Ser
225                 230                 235                 240

Ser Gln Gly Met Gln Arg Met Lys
                245

<210> SEQ ID NO 8
<211> LENGTH: 206
<212> TYPE: PRT
<213> ORGANISM: Murine

<400> SEQUENCE: 8

Glu Asn Met Val Thr Tyr Ser Lys Thr His Gly Val Val Ile Gln Pro
1               5                   10                  15

Ala Tyr Lys Asp Arg Ile Asn Val Thr Glu Leu Gly Leu Trp Asn Ser
                20                  25                  30

Ser Ile Thr Phe Trp Asn Thr His Ile Gly Asp Gly Gly Cys Tyr Met
            35                  40                  45

Cys Leu Phe Asn Thr Phe Gly Ser Gln Lys Val Ser Gly Thr Ala Cys
        50                  55                  60

Leu Thr Leu Tyr Val Gln Pro Ile Val His Leu His Tyr Asn Tyr Phe
65                  70                  75                  80

Glu His His Leu Asn Ile Thr Cys Ser Ala Thr Ala Arg Pro Ala Pro
                85                  90                  95

Ala Ile Thr Trp Lys Gly Thr Gly Thr Gly Ile Glu Asn Ser Thr Glu
                100                 105                 110

Ser His Phe His Ser Asn Gly Thr Thr Ser Val Thr Ser Ile Leu Arg
            115                 120                 125

Val Lys Asp Pro Lys Thr Gln Val Gly Lys Glu Val Ile Cys Gln Val
        130                 135                 140

Leu Tyr Leu Gly Asn Val Ile Asp Tyr Lys Gln Ser Leu Asp Lys Gly
145                 150                 155                 160

Phe Trp Phe Ser Val Pro Leu Leu Leu Ser Ile Val Ser Leu Val Ile
                165                 170                 175

Leu Leu Ile Leu Ile Ser Ile Leu Leu Tyr Trp Lys Arg His Arg Asn
                180                 185                 190

Gln Glu Arg Gly Glu Ser Ser Gln Gly Met Gln Arg Met Lys
            195                 200                 205

<210> SEQ ID NO 9
<211> LENGTH: 268
<212> TYPE: DNA
<213> ORGANISM: Murine

<400> SEQUENCE: 9
atgggcagtc tggtattcag gagacctttc tgccatctct ccacctacag cctgatttgg      60
ggcatagcag cagtagcgct gagcacagct caagtggaag tggtgaccca ggatgaaaga     120
aaggcgctgc acacaactgc atccttacga tgttctctaa aaacatccca ggaacccttg     180
attgtgacat ggcagaaaaa gaaagccgtg agcccagaaa catggtcac ctacagcaaa      240 acccatgggg ttgtaatcca gcctgcct                                        268

<210> SEQ ID NO 10
<211> LENGTH: 256
<212> TYPE: DNA
<213> ORGANISM: Homo sapiens
```

-continued

```
<400> SEQUENCE: 10
gtgatcagga tgcccttctc tcatctctcc tcctacagcc tggtttgggt catggcagca       60
gtggtgctgt gcacagcaca agtgcaagtg gtgacccagg atgaaagaaa ggagctgtac      120
acaactgctt ccttaaaatc ttctcgcaaa aatgcccagg aacgctcgct tgtgacatgg      180
cagaaaaaga aagctgtgag cccagaaaac atggtcacct tcagcgagaa ccatggggtg      240
gtgatccagc ctgcct                                                     256
```

TRUNCATED CD200

FIELD OF THE INVENTION

The present invention relates to a truncated form (termed $CD200_{tr}$) of the immunosuppression-inducing molecule CD200. The $CD200_{tr}$ protein is an antagonist of CD200.

BACKGROUND OF THE INVENTION

The inventor has previously shown that CD200 (OX2) is a powerful immune suppressant and that administering CD200 could inhibit graft rejection and prevent fetal loss and auto immune disease (WO 99/24565, to the present inventor, Gorczynski et al. 1998, 1999a, 1999b, 2000). In particular, the inventor has previously shown that administering antibodies to CD200 inhibited the graft survival generally seen following pre-transplant pv immunization and that administering CD200 inhibits graft rejection. It has also been shown that there is a negative association between levels of CD200 and risk of fetal loss. In particular, administering CD200 reduced fetal loss rates while inhibiting CD200 reversed the effect. The inventor has also shown that administering CD200 prevents autoimmunity. Further, CD200 inhibits cytotoxic cells and IL-2 production and induces IL-4 production. In addition, CD200 is responsible for promoting tumor metastases and inhibiting CD200 reduces tumor cell growth. Recently, Hoek et al. (2000) prepared a CD200 knockout mouse and speculated the role for CD200 in the regulation of cells of the myeloid differentiation pathway and in inflammatory processes within the central nervous system. All of these results demonstrate that CD200 is involved in immune suppression.

The effects of CD200 were reinforced by simultaneous infusion of CD200 receptor ($CD200^r$) bearing cells, and together these data indicate that $CD200:CD200^r$ interactions represented a novel immunoregulatory pathway molecule, which influenced the outcome of TCR:antigen encounter. This immunoregulation was presumed to represent a counter to the immunostimulatory pathways which are triggered after the delivery of costimulatory signals resulting from other ligand:coreceptor interactions, such as those of CD40L with CD40 and CD28 (and CTLA4) with CD80/CD86.

There may be a number of situations wherein it is desirable to inhibit the immune suppressive effects of CD200, for example when immune stimulation (and not suppression) is needed.

SUMMARY OF THE INVENTION

The present inventor has identified a truncated form of CD200, referred to as $CD200_{tr}$ protein herein, that is a physiological antagonist of CD200. The $CD200_{tr}$ protein is a splice variant that lacks exon-2 of the full length CD200 gene. Accordingly, the present invention relates to an isolated $CD200_{tr}$ protein. The invention also includes all uses of the $CD200_{tr}$ protein to modulate CD200 or to inhibit immune suppression caused by CD200. Therefore, modulating CD200 by using the truncated CD200 antagonist has a wide range of applications in transplantation, fetal loss, autoimmunity, tumor immunity, inflammation, neurodegenerative diseases and central nervous system injury and repair.

Accordingly, the present invention provides a method of modulating the activity of CD200 comprising administering an effective amount of a $CD200_{tr}$ protein or a nucleic acid sequence encoding a $CD200_{tr}$ protein to a cell or animal in need thereof.

In one embodiment, the method of the present invention is for inhibiting immunosuppression caused by CD200. Accordingly, the present invention provides a method of inhibiting immune suppression comprising administering an effective amount of a $CD200_{tr}$ protein or a nucleic acid sequence encoding a $CD200_{tr}$ protein to a cell or animal in need thereof.

In another embodiment, the present invention provides a method of enhancing fetal loss comprising administering an effective amount of a $CD200_{tr}$ protein or a nucleic acid molecule encoding a $CD200_{tr}$ protein to an animal in need thereof.

In a further embodiment, the present invention provides a method of enhancing an immune response comprising administering an effective amount of a $CD200_{tr}$ protein or a nucleic acid molecule encoding a $CD200_{tr}$ protein to an animal in need thereof.

In yet another embodiment, the present invention provides a method of inhibiting the growth of a tumor cell comprising administering an effective amount of a $CD200_{tr}$ to a cell or animal in need thereof.

In another embodiment, the present invention provides a method of enhancing immune suppression comprising administering an effective amount of an agent that inhibits a $CD200_{tr}$ protein. Methods of enhancing immune suppression are useful in treating a wide range of conditions including preventing graft rejection, fetal loss, auto immune disease and allergic reactions.

The invention also provides a method of identifying substances which bind with a $CD200_{tr}$ protein, comprising the steps of:

(a) reacting $CD200_{tr}$ protein and a substance, under conditions which allow for formation of a complex, and (b) assaying for complexes, for free substance, and for non-complexed $CD200_{tr}$ protein.

The present invention also includes the $CD200_{tr}$ protein, nucleic acid sequences encoding the $CD200_{tr}$ protein as well as pharmaceutical compositions comprising the $CD200_{tr}$ protein or nucleic acid molecules.

The invention further includes antibodies and antisense oligonucleotides to the $CD200_{tr}$ protein and pharmaceutical compositions comprising the antibodies or oligonucleotides.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1A and SEQ.ID.NO.1 shows the nucleic acid sequence of human CD200.

FIG. 1B and SEQ.ID.NO.2 shows the nucleic acid sequence of human $CD200_{tr}$.

FIG. 2A and SEQ.ID.NO.3 shows the nucleic acid sequence of mouse CD200.

FIG. 2B and SEQ.ID.NO.4 shows the nucleic acid sequence of mouse $CD200_{tr}$.

FIG. 3A and SEQ.ID.NO.5 shows the amino acid sequence of human CD200.

FIG. 3B and SEQ.ID.NO.6 shows the amino acid sequence of human $CD200_{tr}$.

FIG. 4A and SEQ.ID.NO.7 shows the amino acid sequence of mouse CD200.

FIG. 4B and SEQ.ID.NO.8 shows the amino acid sequence of mouse $CD200_{tr}$.

DETAILED DESCRIPTION OF THE INVENTION

I. $CD200_{tr}$

Figure 5:
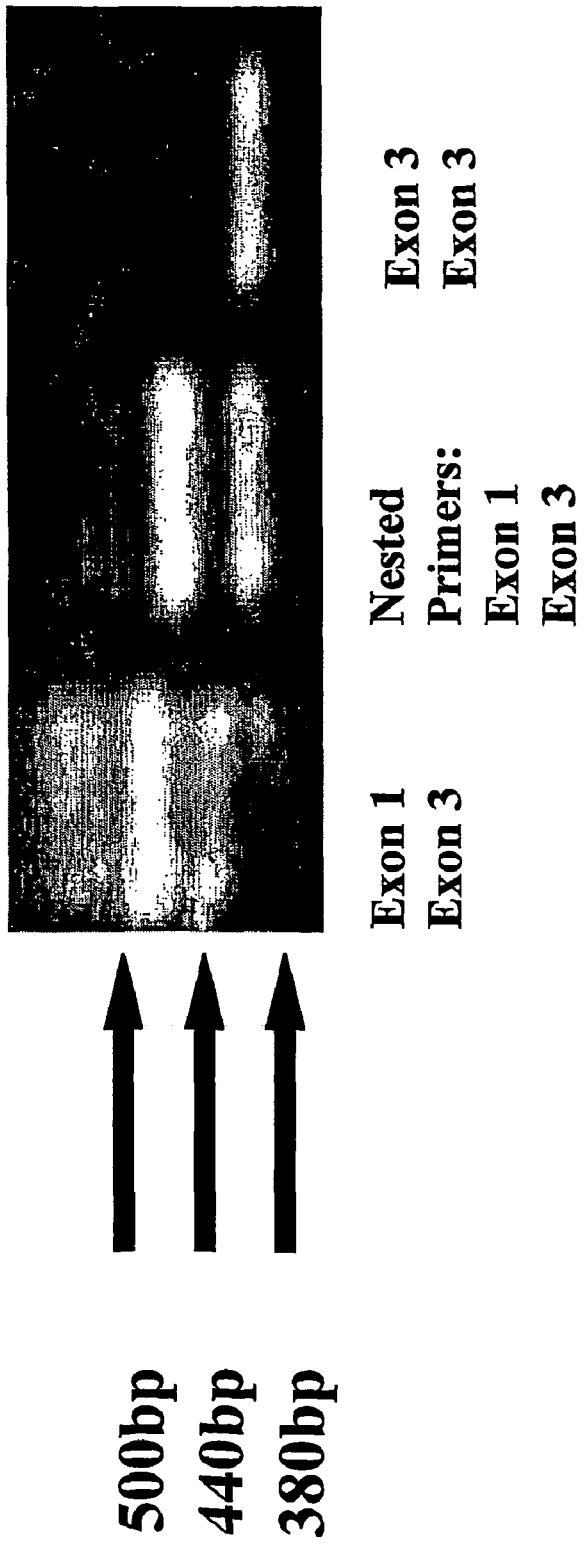
FIG. 5 shows PCR detection of a splice variant of CD200 using cDNA from LPS-stimulated mouse spleen cells. In the first lane, 5' and 3' primers were from exons 1 and 3 of CD200 cDNA. In the second lane nested primers from the same regions were used. In lane 3, both 5' and 3' primers were from exon 3-thus only one band is seen.

The present inventor observed that mRNA extracted from lymphoid tissue of pv immunized mice revealed simultaneous expression of a smaller CD200 mRNA species, corresponding to a splice variant missing exon-2 of the full-length CD200 gene. Sequencing of this mRNA revealed that this splice variant was associated with a frame-shift in translation, and existence of a premature stop codon 20 nt from the 5' end of exon 3 (the V-region exon). Detailed examination of the cDNA sequence of $CD200_{tr}$ protein by the inventor revealed the existence of another consensus Kozak start sequence some 100nt downstream of this stop codon, which corrects the frameshift from the alternate splicing. The inventor assessed whether expression of $CD200_{tr}$ protein from this alternate start codon does occur by expressing the cDNA for either human or mouse $CD200_{tr}$ protein (linked to cDNA encoding green fluorescence protein, GFP) in CHO cells; producing mAbs to $CD200_{tr}$ protein in rats; and staining LPS-stimulated DCs with PE-anti-CD200 and FITC-anti-$CD200_{tr}$ protein. The results are detailed in Example 1 and provide unequivocal proof that in both human and murine cells there is physiological expression of $CD200_{tr}$ protein.

(i) $CD200_{tr}$ Protein

In one aspect, the present invention provides an isolated $CD200_{tr}$ protein.

The term "$CD200_{tr}$ protein" as used herein means a truncated form of the C0200 protein that can antagonize CD200. The $CD200_{tr}$ protein generally lacks exon 2 of the full length CD200 gene. The CD200tr protein can be from any species and can be prepared by one of skill in the art based on the sequence of full length CD200. The amino acid sequence of the human and mouse $CD200_{tr}$ protein is shown in FIGS. 3B (SEQ ID NO: 6) and 4B (SEQ ID NO: 8), respectively. It is to be noted that the term "CD200 protein" or "$CD200_{tr}$ protein" are synonymous with "OX2 protein" or "$OX2_{tr}$ protein", respectively. OX2 was the previous name used for CD200 although due to a change In nomenclature the term CD200 is now more commonly used.

The $CD200_{tr}$ protein may also be obtained from known sources or prepared using recombinant DNA or peptide synthesis techniques. The protein may be prepared using any of the known published sequences for CD200. The sequences can be obtained from GenBank. The human sequence of CD200 has accession no. M17226 X0523; the rat sequence has accession no. X01785; and the mouse sequence of CD200 has accession no. AF029214.

The term "$C200_{tr}$ protein" includes modified forms of the $CD200_{tr}$ protein that also function as an antagonist of CD200. Modified forms of $CD200_{tr}$ include analogs and derivatives of $CD200_{tr}$ protein.

The term "analog" includes any peptide having an amino acid residue sequence substantially identical to the $CD200_{tr}$ protein sequence shown in FIG. 3B (SEQ ID NO: 6) or 4B (SEQ ID NO: 8) in which one or more residues have been conservatively substituted with a functionally similar residue and which displays the ability to antagonize CD200 as described herein. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that such polypeptide displays the requisite activity.

The term "derivative" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycaibonyl groups, chioroacetyl groups or fonnyl groups. Free carboxyl groups may be derivatized to form salts, methyl and ethyl esters or other types of esters or hydrazides. Free hydroxyl groups may be derivatized to form O acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. $CD200_{tr}$ proteins of the present invention also include any polypeptide having one or more additions and/or deletions or residues relative to the sequence of the $CD200_{tr}$ protein shown in FIG. 3B (SEQ ID NO: 6) or 4B (SEQ ID NO: 8), so long as the requisite activity is maintained.

The $CD200_{tr}$ protein may be prepared as a soluble fusion protein. The fusion protein may contain the extracellular domain of $CD200_{tr}$ protein linked to an immunoglobulin (Ig) Fc Region. The $CD200_{tr}$ protein fusion may be prepared using techniques known in the art Generally, a DNA sequence encoding the extracellular domain of $CD200_{tr}$ protein is linked to a DNA sequence encoding the Fc of the Ig and expressed in an appropriate expression system where the $CD200_{tr}$ protein—FcIg fusion protein is produced. The $CD200_{tr}$ protein may be prepared using recombinant DNA techniques.

The $CD200_{tr}$ protein may be modified to make it more therapeutically effective or suitable. For example, the $CD200_{tr}$ protein may be cyclized as cyclization allows a peptide to assume a more favourable conformation. Cyclization of the $CD200_{tr}$ protein peptides may be achieved using techniques known in the art. In particular, disulphide bonds may be formed between two appropriately spaced components having free sulfhydryl groups. The bonds may be formed between side chains of amino acids, non-amino acid components or a combination of the two. In addition, the $CD200_{tr}$ protein or peptides of the present invention may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and tolunesulphonic acids.

(ii) $CD200_{tr}$ Nucleic Acid

In another aspect, the present invention also includes all nucleic acid sequences encoding the CD200t, protein of the invention. The nucieic acid sequence encoding the human and mouse CD200fr protein is shown in FIGS. 1B (SEQ ID NO: 2) and 2B (SEQ ID NO: 4), respectively.

In a preferred embodiment, the nucleic acid molecule encoding the $CD200_{tr}$ protein comprises:

(a) a nucleic acid sequence as shown in FIG. 1B (SEQ ID NO: 2) or 2B (SEQ ID NO: 4) wherein T can also be U;

(b) a nucleic acid sequence that is complimentary to a nucleic acid sequence of (a):

(c) a nucleic acid sequence that has substantial sequence homology to a nucleic acid sequence of (a) or (b);

(d) a nucleic acid sequence that is an analog of a nucleic acid sequence of (a), (b) or (c); or (e) a nucleic acid sequence that hybridizes to a nucleic acid sequence of (a), (b), (c) or (d) under stringent hybridization conditions.

The term "sequence that has substantial sequence homology" means those nucleic acid sequences which have slight or inconsequential sequence variations from the sequences in (a) or (b), i.e., the sequences function in substantially the same manner and encodes a protein that is capable of inhibiting the activity of CD200. The variations may be attributable to local mutations or structural modifications. Nucleic acid sequences having substantial homology include nucleic acid sequences having at least 65%, more preferably at least 85%, and most preferably 90–95% identity with the nucleic acid sequences as shown in FIG. 1B (SEQ ID NO: 2) or 2B (SEQ ID NO: 4).

The term "sequence that hybridizes" means a nucleic acid sequence that can hybridize to a sequence of (a), (b), (c) or (d) under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1–6.3.6. For example, the following may be employed: 6.0×sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

The term "a nucleic acid sequence which is an analog" means a nucleic acid sequence which has been modified as compared to the sequence of (a), (b) or (c) wherein the modification does not alter the utility of the sequence (i.e. as encoding a protein that inhibits CD200) as described herein. The modified sequence or analog may have improved properties over the sequence shown in (a). (b) or (c). One example of a modification to prepare an analog is to replace one of the naturally occurring bases (i.e. adenine, guanine, cytosine or thymidine) of the sequence shown in FIG. 1B (SEQ ID NO: 2) or 2B (SEQ ID NO: 4) with a modified base such as such as xanthine, hypoxanthine, 2-aminoadenine, 6-methyl, 2-propyl and other alkyl adenines, 5-halo uracil, 5-halo cytosine, 6-aza uracil, 6-era cytosine and 6-an thymine, pseudo uracil, 4-thiouracil, 8-halo adenine, 8-aminoadenine, 8-thiol adenine, 8-thiolalkyl adenines, 8-hydroxyl adenine and other 8-substituted aderiines, 8-halo guanines, 8 amino guanine, 8-thiol guanine, 8-thiolalkyl guanines, 8-hydroxyl guanine and other 8-substituted guanines. other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in FIG. 1B (SEQ ID NO: 2) or 2B (SEQ ID NO: 4). For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extend d lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

(iii) Antibodies

The present invention further includes antibodies to the CD200$_{tr}$ protein. The inventor has prepared antibodies to CD200$_{tr}$ protein which are described in Example 1. Antibodies to CD200$_{tr}$ protein may also be prepared using techniques known in the art such as those described by Kohler and Milstein, Nature 256, 495 (1975) and in U.S. Patent. No. RE 32,011; U.S. Pat. Nos. 4,902,614; 4,543,439; and 4,411,993, which are incorporated herein by reference. (See also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference). Within the context of the present invention, antibodies are understood to include monoclonal antibodies, polyclonal antibodies, antibody fragments (e.g., Fab, and F(ab')2) and recombinantly produced binding partners.

(iv) Antisense Oligonucleotides

The invention also includes antisense oligonucleotides that inhibit the expression of CD200$_{tr}$ protein. The term antisense oligonucleotide as used herein means a nucleotide sequence that is complimentary to its target.

In one embodiment of the invention, the present invention provides an antisense oligonucleotide that is complimentary to a nucleic acid molecule having a sequence as shown in FIG. 1B (SEQ ID NO: 2) or 2B (SEQ ID NO: 4), wherein T can also be U, or a fragment thereof.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

(v) CD200$_{tr}$ Ligands

The present invention also includes the isolation of other ligands or molecules that can bind to the CD200$_{tr}$ protein. Biological samples and commercially available libraries may be tested for proteins that bind to the CD200$_{tr}$ protein. In addition, the above described antibodies to the CD200$_{tr}$ protein may be used to isolate other peptides with CD200$_{tr}$ protein binding affinity. For example, labelled antibodies may be used to probe phage displays libraries or biological samples.

Conditions which permit the formation of protein complexes may be selected having regard to factors such as the nature and amounts of the substance and the protein.

The substance-protein complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, the antibodies, proteins, or substances may be labelled with a detectable substance.

Once potential binding partners have been isolated, screening methods may be designed in order to determine if the molecules that bind to the CD200$_{tr}$ peptide are useful in modulating the activity of CD200.

Therefore, the invention also provides methods for identifying substances which are capable of binding to the CD200$_{tr}$ protein. In particular, the methods may be used to identify substances which are capable of binding to and augmenting or attenuating the effects of the CD200$_{tr}$ protein or which suppress the effects of the CD200$_{tr}$ protein. Accordingly, the invention provides a method of identifying substances which bind with a CD200$_{tr}$ protein, comprising the steps of:

(a) reacting CD200$_{tr}$ protein and a substance, under conditions which allow for formation of a complex, and (b) assaying for complexes, for free substance, and for non-complexed CD200$_{tr}$ protein.

Substances which can bind with the CD200$_{tr}$ of the invention may be identified by reacting CD200$_{tr}$ with a substance which potentially binds to the CD200$_{tr}$ and assaying for complexes, for free substance, or for non-complexed CD200$_{tr}$. Any assay system or testing method that detects protein-protein interactions may be used including co immunoprecipitation, crosslinking and co-purification through gradients or chromatographic columns may be used. Additionally, x-ray crystallographic studies may be used as a means of evaluating interactions with substances and molecules. For example, purified recombinant molecules in a complex of the invention when crystallized in a suitable form are amenable to detection of intra-molecular interactions by x-ray crystallography. Spectroscopy may also be used to detect interactions and in particular, Q-TOF instrumentation may be used. Biological samples and commercially available libraries may be tested for CD200-binding peptides. In addition, antibodies prepared to the peptides of the invention may be used to isolate other peptides with CD200$_{tr}$ binding affinity. For example, labelled antibodies may be used to probe phage display libraries or biological samples. In this respect peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al. 1992, J. Mol. Biol. 227: 711; Devlin et al., 1990 Science 249:404; Cwirla et al. 1990, Proc. Natl. Acad, Sci. USA, 87:6378). Libraries may also be constructed by concurrent synthesis of overlapping peptides (see U.S. Pat. No. 4,708,871).

It will be understood that the agonist and antagonist that can be assayed using the methods of the invention may act on one or more of the binding sites on the protein or substance including agonist binding sites, competitive antagonist binding sites, non-competitive antagonist binding sites or allosteric sites.

The invention also makes it possible to screen for antagonists that inhibit the effects of an agonist of the interaction of $CD200_{tr}$ with a substance which is capable of binding to $CD200_{tr}$. Thus, the invention may be used to assay for a substance that competes for the same binding site of $CD200_{tr}$. As such it will also be appreciated that intracellular substances which are capable of binding to $CD200_{tr}$ may be identified using the methods described herein.

The reagents suitable for applying the methods of the invention to evaluate substances and compounds that affect or modulate a $CD200_{tr}$ may be packaged into convenient kits providing the necessary materials packaged into suitable containers. The kits may also include suitable supports useful in performing the methods of the invention.

II. Therapeutic Methods (i) Methods of Preventing Immune Suppression

The present inventor has demonstrated that the $CD200_{tr}$ protein can antagonize the immune suppression induced by CD200. In particular, the inventor demonstrates in Example 1 that both CHO cells and DCs, when transduced to express $CD200_{tr}$, protein antagonize the immunosuppression induced by the homologous soluble form of CD200 (CD200: Fc) in mixed leukocyte cultures (MLC) in vitro. These data imply a potentially important role for regulation of relative expression of $CD200/CD200_{tr}$ protein in the immunosuppression induced by $CD200:CD200^r$ interactions.

Accordingly, the present invention provides a method of modulating the activity of CD200 comprising administering an effective amount of a $CD200_{tr}$ protein or a nucleic acid sequence encoding a $CD200_{tr}$ protein to a cell or animal in need thereof.

The term "effective amount" as used herein means an amount effective, at dosages and for periods of time necessary to achieve the desired result, for example to modulate, reduce, inhibit and/or prevent the immune suppression caused by CD200.

The term "animal" as used herein includes all members of the animal kingdom including humans.

The term "administering a $CD200_{tr}$ protein" includes both the administration of the $CD200_{tr}$ protein as well as the administration of a nucleic acid sequence encoding a $CD200_{tr}$ protein. In the latter case, the $CD200_{tr}$ protein is produced in vivo in the cell or animal.

In a preferred embodiment, the $CD200_{tr}$ protein is prepared and administered as a soluble fusion protein. Soluble fusion proteins can be prepared using techniques known in the art. As an example, the fusion protein may contain the extracellular domain of $CD200_{tr}$ linked to an immunoglobulin (Ig) Fc region or to any other intracellular domain. The CD200:Fc fusion may be prepared using techniques known in the art. Generally, a DNA sequence encoding the extracellular domain of $CD200_{tr}$ is linked to a DNA sequence encoding the Fc of the Ig and expressed in an appropriate expression system where the $CD200_{tr}$-FcIg fusion protein is produced.

As the $CD200_{tr}$ protein is an antagonist of CD200, it can be used to treat any condition wherein it is desirable to inhibit or counter the immune suppressive effects of CD200. In one embodiment, the method of the present invention is for inhibiting immunosuppression caused by CD200. Accordingly, the present invention provides a method of inhibiting immune suppression comprising administering an effective amount of a $CD200_{tr}$ protein or a nucleic acid sequence encoding a $CD200_{tr}$ protein to a cell or animal in need thereof. The present invention also provides a use of a $CD200_{tr}$ protein or a nucleic acid encoding a $CD200_{tr}$ protein to inhibit immune suppression or to prepare a medicament to inhibit immune suppression.

On of skill in the art can readily determine whether or not a particular $CD200_{tr}$ is effective in inhibiting CD200. For example, the $CD200_{tr}$ can be tested in in vitro assays to determine if the function or activity of CD200 is inhibited.

It has been demonstrated that there is an association between levels of CD200 expression and fetal loss. In particular, low levels of CD200 is correlated to fetal loss (see WO 99/24565 to the present inventor). As a result, inhibiting CD200 with $CD200_{tr}$ protein may induce fetal loss. Accordingly, in another embodiment, the present invention provides a method of inducing fetal loss comprising administering an effective amount of a $CD200_{tr}$ protein or a nucleic acid molecule encoding a $CD200_{tr}$ protein to an animal in need thereof. The present invention also provides a use of a $CD200_{tr}$ protein or a nucleic acid encoding a $CD200_{tr}$ protein to induce fetal loss or to prepare a medicament to induce fetal loss.

One of skill in the art can determine whether a particular $CD200_{tr}$ is useful in inducing fetal loss. As mentioned above, one can test the $CD200_{tr}$ for its ability to induce an immune response or to prevent immune suppression using known in vitro assays. In addition, the $CD200_{tr}$ protein can be tested in an animal model wherein it is administered to a pregnant non-human animal such as a rodent.

As CD200 is a potent immune suppressant, administering $CD200_{tr}$ protein may act to enhance the immune response and may be useful in treating several diseases including infections, immune deficiencies (including AIDS) and cancer. Administering $OX_{tr}$ may also be beneficial in accelerating wound healing and the repair of damage to the central nervous system. Accordingly, in a further embodiment, the present invention provides a method of enhancing an immune response comprising administering an effective amount of a $CD200_{tr}$ protein or a nucleic acid molecule encoding a $CD200_{tr}$ protein to an animal in need thereof. The present invention also provides a use of a $CD200_{tr}$ protein or a nucleic acid encoding a $CD200_{tr}$ protein to enhance an immune response or to prepare a medicament to enhance an immune response.

The term "immune response" includes any response of the immune system including both non-specific and specific responses. Specific responses include both cell-mediated (e.g. T cell) and humoral (antibody) responses.

A $CD200_{tr}$ can be tested for its ability to induce an immune response using in vitro immune assays including, but not limited to, enhancing a cytotoxic T cell response;

inducing interleukin-2 (IL-2) production; inducing IFNγ production; inducing a Th1 cytokine profile; inhibiting IL4 production; inhibiting TGFβ production; inhibiting IL-10 production; inhibiting a Th2 cytokine profile and any other assay that would be known to one of skill in the art to be useful in detecting immune activation.

As mentioned previously, the invention has shown that inhibiting CD200 inhibits tumor growth. Accordingly, the present invention provides a method of inhibiting, preventing or reducing tumor cell growth comprising administering an effective amount of a $CD200_{tr}$ protein or a nucleic acid molecule encoding a $CD200_{tr}$ protein to an animal in need thereof. The present invention also provides a use of a $CD200_{tr}$ protein or a nucleic acid encoding a $CD200_{tr}$ protein to inhibit or reduce tumor growth or to prepare a medicament to inhibit or reduce tumor growth.

The term "inhibiting or reducing tumor cell growth" means that the $CD200_{tr}$ causes an inhibition or reduction in the growth or metastasis of a tumor as compared to the growth observed in the absence of the $CD200_{tr}$. The $CD200_{tr}$ may also be used prophylactically to prevent the growth of tumor cells. The ability of a CD200tr to inhibit tumor cell growth can be assessed in in vitro and in vivo assays known in the art. For example, the $CD200_{tr}$ can be administered to cancer cells in vitro or in vivo to an animal with cancer and the effects of the $CD200_{tr}$ on tumor growth can be assessed.

The method can be used to treat any type of cancer, including, but not limited to, leukemias, lymphomas (Hodgkins and non-Hodgkins), plasmacytomas, histiocytomas, melanomas, adenomas, sarcomas, carcinomas of solid tissues, hypoxic tumours, squamous cell carcinomas, genitourinary cancers such as cervical and bladder cancer, hematopoietic cancers, head and neck cancers, and nervous system cancers.

In another embodiment, the present invention provides a method of treating an infectious disease comprising administering an effective amount of a $CD200_{tr}$ protein or a nucleic acid molecule encoding a $CD200_{tr}$ protein to an animal in need thereof. The infectious disease can be any disease caused by a pathogen such as viruses, bacteria, fungi, mycoplasms, parasites. In one embodiment, the infectious disease is sepsis.

In a further embodiment, the present invention provides a method of treating a wound comprising administering an effective amount of a $CD200_{tr}$ protein or a nucleic acid molecule encoding a $CD200_{tr}$ protein to an animal in need thereof. The invention also includes a use of a $CD200_{tr}$ protein or a nucleic acid encoding a $CD200_{tr}$ protein to treat a wound or to prepare a medicament to treat a wound.

In another embodiment, the present invention provides a method of treating an injury of the nervous system comprising administering an effective amount of a $CD200_{tr}$ protein or a nucleic acid molecule encoding a $CD200_{tr}$ protein to an animal in need thereof. The invention also includes a use of a $CD200_{tr}$ protein or a nucleic acid encoding a $CD200_{tr}$ protein to treat an injury of the nervous system or to prepare a medicament to treat an injury of the nervous system.

(ii) Methods of Enhancing Immune Suppression

As the $CD200_{tr}$ protein is an antagonist of CD200, inhibiting the $CD200_{tr}$ protein or gene may be useful in enhancing the immune suppression regulated by CD200.

Accordingly, the present invention provides a method of enhancing immune suppression comprising administering an effective amount of an agent that inhibits a $CD200_{tr}$ protein to a cell or animal in need thereof. The invention also includes a use of an agent that inhibits a $CD200_{tr}$ protein to enhance immune suppression or to prepare a medicament to enhance immune suppression.

The term "enhancing immune suppression" means that an immune response observed in the presence of the agent that inhibits a $CD200_{tr}$ protein is lower than the immune observed in the absence of the agent. Methods for determining whether immune suppression occurs are known in the art and described herein.

The term "agent that inhibits a $CD200_{tr}$ protein" includes any agent that can inhibit, prevent or reduce the antagonistic or inhibitory effects of $CD200_{tr}$ on CD200 induced immune suppression. Agents that inhibit a $CD200_{tr}$ protein include antibodies that can block the activity of the protein, antisense molecules that can inhibit expression of the protein and other molecules or ligands identified using the screening assays described herein. Antibodies and antisense molecules to $CD200_{tr}$ protein are described above.

Determining whether a particular agent is useful in inhibiting $CD200_{tr}$ can be assessed using techniques known to one of skill in the art. In particular one can develop an assay wherein the effect of $CD200_{tr}$ on CD200 mediated immune suppression is compared to the effect of $CD200_{tr}$ in the presence of the agent to be tested for inhibitory activity. Where the $CD200_{tr}$ no longer prevents CD200 mediated immune suppression, the agent can be said to inhibit $CD200_{tr}$. Determining whether CD200 can exert its immune suppressive effects can be assessed using known in vitro immune assays including, but not limited to, inhibiting a mixed leucocyte reaction; inhibiting a cytotoxic T cell response; inhibiting interleukin-2 production; inhibiting IFNγ production; inhibiting a Th1 cytokine profile; inducing IL-4 production; inducing TGFβ production; inducing IL-10 production; inducing a Th2 cytokine profile; and any other assay that would be known to one of skill in the art to be useful in detecting immune suppression.

Conditions wherein it would be desirable to enhance immune suppression include the induction of immune tolerance and the treatment or prevention of transplant rejection, graft versus host disease, auto immune disease, allergy, fetal loss, inflammation, neurodegeneration, artherosclerosis, vasculitides, delayed hypersensitivities, stroke, spinal injury and ischemia.

In particular, the inventor has previously shown that administering CD200 inhibits graft rejection. Accordingly, inhibiting the antagonizing effects of $CD200_{tr}$ may be useful in prolonging graft survival.

In one embodiment, the present invention provides a method of preventing rejection of a transplant or graft in a recipient animal comprising administering an effective amount of an agent that inhibits a $CD200_{tr}$ protein to the recipient animal. The invention also includes a use of an agent that inhibits $CD200_{tr}$ to prevent graft rejection or to prepare a medicament to prevent graft rejection.

The recipient can be any member of the animal kingdom including rodents, pigs, cats, dogs, ruminants, non-human primates and preferably humans. The organ or tissue to be transplanted can be from the same species as the recipient (allograft) or can be from another species (xenograft). The tissues or organs can be any tissue or organ including heart, liver, kidney, lung, pancreas, pancreatic islets, brain tissue, cornea, bone, intestine, skin and heamatopoietic cells.

The method of the invention to enhance immune suppression may also be used to prevent graft versus host disease wherein the immune cells in the transplant mount an immune attack on the recipient's immune system. This can occur when the tissue to be transplanted contains immune cells such as when bone marrow or lymphoid tissue is transplanted when treating leukemias, aplastic anemias and enzyme or immune deficiencies, for example. Accordingly, the present invention provides a method of preventing or inhibiting graft versus host disease comprising administering an effective amount of an agent that inhibits a $CD200_{tr}$ protein to an animal in need thereof. The invention also includes a use of an agent that inhibits $CD200_{tr}$ protein to prevent or inhibit graft versus host disease or to prepare a medicament to prevent graft versus host disease.

The method of the present invention to enhance immune suppression may also be used to treat or prevent auto immune disease. The inventor has previously shown that administering CD200 is useful in preventing auto immune disease. Therefore, inhibiting the $CD200_{tr}$ protein may be useful in treating auto immune disease. Accordingly, the present invention provides a method of treating or preventing an auto immune disease comprising administering an effective amount of an agent that inhibits a $CD200_{tr}$ protein to an animal in need thereof. The invention also includes a use of an agent that inhibits $CD200_{tr}$ protein to prevent auto immune disease or to prepare a medicament to prevent auto immune disease.

Autoimmune diseases that may be treated or prevented according to the present invention include, but are not limited to, type 1 insulin-dependent diabetes mellitus, adult respiratory distress syndrome, inflammatory bowel disease, dermatitis, meningitis, thrombotic thrombocytopenic purpura, Sjögren's syndrome, encephalitis, uveitic, leukocyte adhesion deficiency, rheumatoid arthritis, rheumatic fever, Reiter's syndrome, psoriatic arthritis, progressive systemic sclerosis, primary biniary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, auto immune haemolytic anemia, Hashimoto's thyroiditis, Graves disease, habitual spontaneous abortions, Reynard's syndrome, glomerulonephritis, dermatomyositis, chronic active hepatitis, celiac disease, auto immune complications of AIDS, atrophic gastritis, ankylosing spondylitis and Addison's disease.

The method of the present invention to enhance immune suppression may also be used to treat or prevent an allergic reaction. In an allergic reaction, the immune system mounts an attack against a generally harmless, innocuous antigen or allergen. Accordingly, the present invention provides a method of treating or preventing an allergic reaction comprising administering an effective amount of an agent that inhibits a $CD200_{tr}$ protein to an animal in need thereof. The invention also includes a use of an agent that inhibits a $CD200_{tr}$ protein to treat or prevent an allergic reaction or to prepare a medicament to treat or prevent an allergic reaction.

Allergies that may be prevented or treated using the methods of the invention include, but are not limited to, hay fever, asthma, atopic eczema as well as allergies to poison oak and ivy, house dust mites, bee pollen, nuts, shellfish, penicillin and numerous others.

Generally, inhibiting the $OX_{tr}$ protein can be used to treat any inflammatory condition wherein it is desirable to suppress the immune response. Accordingly, the present invention provides a method of treating an inflammatory condition comprising administering an effective amount of an agent that inhibits a $CD200_{tr}$ protein to an animal in need thereof. The invention also includes a use of an agent that inhibits a $CD200_{tr}$ protein to treat an inflammatory condition or to prepare a medicament to treat an inflammatory condition.

The $OX_{tr}$ protein may also be used to treat a neurodegenerative disease or condition. Accordingly, the present invention provides a method of treating a neurodegenerative disease or condition comprising administering an effective amount of an agent that inhibits a $CD200_{tr}$ protein to an animal in need thereof. The invention also includes a use of an agent that inhibits a $CD200_{tr}$ protein to treat a neurodegenerative disease or condition or to prepare a medicament to treat a neurodegenerative disease or condition. Examples of neurodegenerative diseases or conditions include Alzheimer's disease, Parkinson's disease, Pick's disease, amyotrophic lateral sclerosis, Huntington's disease, stroke, head trauma, Bell's palsy, spinal cord and other nerve crush injuries, multiple sclerosis, cardiac myopathies, nephropathy, retinopathy, diabetic complications, glaucoma, idiopathic neuropathies as well as any condition wherein there is a degeneration of cells. The methods of the invention may also be used prophylactically to prevent premature degeneration of cells.

The inventor has previously shown that administering CD200 can prevent fetal loss. Therefore, the method of the present invention to enhance immune suppression may also be used to treat or prevent fetal loss including the treatment of habitual miscarriages, pre-eclampsia and pre-term labour. Accordingly, the present inventor provides a method of preventing fetal loss comprising administering an effective amount of an agent that inhibits $CD200_{tr}$ to an animal in need thereof. The invention also includes a use of an agent that inhibits a $CD200_{tr}$ protein to prevent fetal loss or to prepare a medicament to prevent fetal loss.

One of skill in the art can also determine whether or not a particular agent that inhibits $CD200_{tr}$ is useful in preventing fetal loss. For example, one of skill in the art can readily test an agent for its ability to prevent CD200 inhibition by testing the ability of CD200 to suppress an immune response using known in vitro assays. In addition the agent can also be tested for its ability to prevent fetal loss in an animal model. For example, one could use a model wherein the ability of $CD200_{tr}$ to prevent cytokine induced abortion in abortion-prone CBA×DBA/2 mice is assessed. Further, mice pre-immunized with anti-phospholipid may also be used.

III. Compositions

The invention also includes pharmaceutical compositions containing $CD200_{tr}$ proteins or nucleic acids for use in preventing immune suppression as well as pharmaceutical compositions containing agents that inhibit $CD200_{tr}$ proteins for use in enhancing immune suppression. The pharmaceutical composition may also contain molecules that bind $CD200_{tr}$ proteins including agonists or antagonists identified using the screening methods described herein.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions.

The pharmaceutical compositions of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as immunosuppressive drugs or antibodies to enhance immune tolerance or immunostimulatory agents to enhance the immune response.

In one embodiment, the pharmaceutical composition for use in preventing immune suppression comprises an effective amount of a $CD200_{tr}$ protein or a nucleic acid encoding a $CD200_{tr}$ protein in admixture with a pharmaceutically acceptable diluent or carrier. The $CD200_{tr}$ protein is preferably prepared as an immunoadhesion molecule in soluble form which can be administered to the patient. The $CD200_{tr}$ may also be co-administered with other agents capable of enhancing an immune response including cytokines, adjuvants, other immune modulators including $CD200^r$, MD-1 (see WO 01/68697 to the present inventor), CD80, CD86, CD40, B7n, LIGHT and/or by administering cross linking ligands or antibodies to their receptors.

The nucleic acid molecules of the invention encoding a $CD200_{tr}$ protein may be used in gene therapy to prevent immune suppression or enhance an immune response. In addition, antisense nucleic acid molecules to $CD200_{tr}$ may be used in gene therapy to enhance immune suppression. Recombinant molecules comprising a nucleic acid sequence encoding a $CD200_{tr}$ protein or an antisense oligonucleotide to $CD200_{tr}$ may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage. The nucleic acid molecules of the invention may also be applied extracellularly such as by direct injection into cells. The nucleic acid molecules encoding $CD200_{tr}$ protein are preferably prepared as a fusion with a nucleic acid molecule encoding an immunoglobulin (Ig) Fc region. As such, the $CD200_{tr}$ protein will be expressed in vivo as a soluble fusion protein.

In another embodiment, the pharmaceutical composition for use in inducing immune suppression comprises an effective amount of an agent that inhibits a $CD200_{tr}$ protein in admixture with a pharmaceutically acceptable diluent or carrier. The pharmaceutical composition may also contain other immune suppressants including cyclosporin, immune suppressive molecules including CD200 and antagonists of immune stimulatory molecules including MD-1 antagonists. When treating an inflammatory condition the $CD200_{tr}$ can be co-administered with an anti-inflammatory agent, an analgesic or a steroid.

The following non-limiting examples are illustrative of the present invention:

EXAMPLE

Example 1

Materials and Methods

Mice: Male C3H/HEJ and C57BL/6 mice were purchased from the Jackson laboratories, Bar Harbour, Me. Mice were housed 5/cage and allowed food and water ad libitum. All mice were used at 8–12 weeks of age. Lewis rats (LEW) were obtained at 8 weeks of age from Sprague Dawley.

Monoclonal antibodies: The following monoclonal antibodies (mAbs) were obtained from Pharmingen (San Diego, Calif., USA) unless stated otherwise: anti-IL-2 (S4B6, ATCC; biotinylated JES6-5H4); anti-IL-4 (11B11, ATCC; biotinylated BVD6-24G2); anti-IFNγ (R4-6A2, ATCC; biotinylated XMG1.2); anti-IL-10 (JES5-2A5; biotinylated, SXC-1); anti-IL-6 (MP5-20F3; biotinylated MP5-32C11); anti-TNFα (G281-2626; biotinylated MP6XT3); FITC anti-CD80, FITC anti-CD86, FITC anti-CD40, L3T4 (anti-mouse CD4), anti-thy1.2 and anti-Ly2.2 were obtained from Cedarlane Labs, Hornby, Ontario. The hybridoma producing DEC205 (anti-mouse dendritic cells) was a kind gift from Dr. R. Steinman, and was directly labeled with FITC; PE-conjugated rat anti-mouse CD200 (3B6) and anti-human CD200 (A9A2) was obtained from BioSpark Inc., Mississauga, Ontario, Canada. FITC conjugation of rat anti-$CD200_{tr}$ was performed following standard protocols.

Strepavidin horse radish peroxidase and recombinant mouse GM-CSF was purchased from Pharmingen (San Diego, Calif.).

Preparation of cells: Single cell spleen suspensions were prepared aseptically from pools of stock mice and after centrifugation cells were resuspended in α-Minimal Essential Medium supplemented with 2-mercaptoethanol and 10% fetal calf serum (αF10). LPS splenic DC, stained (>90%) with DEC205, were obtained by overnight culture (1 μg/ml LPS) of adherent fresh spleen cells as described by Steinman et al. Human DCs were obtained by similar overnight culture of adherent PBL obtained following hypaque purification of cells from volunteer donors.

Portal Vein (pv) Immunization with Dendritic Cells (DC) was Performed as Described Earlier:

Bone marrow derived dendritic cells (DC) for pv immunization were obtained by culture for 7 days of L3T4, anti-thy1.2, anti-Ly2.2 treated mouse bone marrow cells in the presence of 500U/ml GM-CSF. An aliquot of the sample stained with FITC conjugated DEC205 mAb showed a mean staining in the order of 91%±8%.

Stable Transduction of CHO Cells Expressing $CD200_{tr}$ and Production of Anti-$CD200_{tr}$ mAbs:

RT-PCR using RNA extracted from LPS stimulated splenic adherent cells and 5'/3' primers for full-length CD200 cDNA reveals two mRNA species of ~800 bp (encoding full-length CD200) and ~700 bp respectively (see FIG. 5). The latter encodes a splice variant missing exon 2 of the full-length mRNA species, and following initiation of translation in exon 1 is associated with a premature stop codon in exon 3. However a second ATG start codon some 100 bp downstream could theoretically lead to expression of a truncated form of CD200 ($CD200_{tr}$) from this mRNA (FIGS. 1 (SEQ ID NOs:1 and 2) and 2 (SEQ ID NOs: 3 and 4) for human and mouse, respectively). The cDNA sequences of the 5' ends of the full-length and putative truncated forms are shown with the premature (out-offrame, for CD200) stop codon (bold) and alternate translational ATG start codon in CD200$_{tr}$ underlined below.

```
Mouse CD200 leader sequence
                                                            (SEQ ID NO:9)
ATGGGCAGTCTGGTATTCAGGAGACCTTTCTGCCATCTCTCCACCTACAGCCTGATTTGGGGCATAG 67

|V-like domain--
CAGCAGTAGCGCTGAGCACAGGTCAAGTGGAAGTGGTGACCCAGGATGAAAGAAAGGCGCTGCACAC 134

AACTGCATCCTTACGATGTTCTCTAAAAACATCCCAGGAACCCTTGATTGTGACATGGCAGAAAAG 201

AAAGCCGTGAGCCCAGAAAACATGGTCACCTACAGCAAAACCCATGGGGTTGTAATCCAGCCTGCCT 268

Human CD200 leader sequence
                                                           (SEQ ID NO:10)
GTGATCAGGATGCCCTTCTCTCATCTCTCCTCCTACAGCCTGGTTTGGGTCATGG              55

|V-like domain--
CAGCAGTGGTGCTGTGCACAGCACAAGTGCAAGTGGTGACCCAGGATGAAAGAAAGGAGCTGTACAC 122

AACTGCTTCCTTAAAATCTTCTCGCAAAAATGCCCAGGAACGCTCGCTTGTGACATGGCAGAAAAAG 189

AAAGCTGTGAGCCCAGAAAACATGGTCACCTTCAGCGAGAACCATGGGTGGTGATCCAGCCTGCCT
``` cDNAs for the splice variants of both human and murine CD200$_{tr}$ were constructed with 5'/3' primer pairs selected to introduce BamH1 and EcoR1 cloning sites at the ends. The amplicons were ligated into the PEGFP-N2 cloning vector (CloneTech) and kanamycin-resistant colonies selected after transformation of DH5α cells. Plasmid DNA was extracted for transfection of CHO cells using 1 μg cDNA and 2.5 μl Lipofectamine 2000 (GIBCO BRL). GFP fusion protein expression was assessed by florescence microscopy, with transfection efficiency routinely ~50–70%. 48 h after transfection cells were selected with 500 μg/ml G418(GIBCO BRL). At 10 days cells were sorted to select GFP positive cells, the insert confirmed by RT-PCR, and the CD200$_{tr}$- positive cells expressing the GFP fusion protein recloned. Several clones with 98%–100% fluorescent cells were identified. Cells from one each of the clones expressing human or murine CD200$_{tr}$ were used to immunize 3 Lewis rats of each group ip (10×10$^6$ cells/injection)×3 at 2-week intervals in 0.2 ml Complete Freunds Adjuvant. Thereafter spleen cells within the two different immunized rat groups were pooled, and an aliquot of each cells fused with the rat hybridoma parent cell line YB2/0, as described earlier. Supernatants of hybridoma secreting cells were screened by FACS for staining of CHO transduced with human or mouse CD200$_{tr}$. Positive hybridoma cells were recloned, aliquots frozen in liquid nitrogen, and the supernatants used for further characterization (see below).

Cytotoxicity and Cytokine Assays:

In allogeneic mouse mixed leukocyte cultures (MLC) used to assess cytokine production C3H responder cells were stimulated with equal numbers of mitomycin-C treated (45 min at 37° C.) C57BL/6 spleen stimulator cells in triplicate in αF10. Supernatants were pooled at 40 hr from replicate wells and assayed in triplicate in ELISA assays or bioassays for lymphokine production as described below.

All cytokines were measured in ELISA assays, with capture and biotinylated detection mAbs as described above. Varying volumes of supernatant were bound in triplicate at 4° C. to plates pre-coated with 100 ng/ml mAb, washed×3, and biotinylated detection antibody added. After washing, plates were incubated with strepavidin-horse radish peroxidase (Cedarlane Labs), developed with appropriate substrate and OD$_{405}$ determined using an ELISA plate reader. Recombinant cytokines for standardization were obtained from Pharmingen (U.S.A.). All assays showed sensitivity in the range 40 to 4000 pg/ml. Where cytotoxicity was assayed, cells were harvested from MLC at 5 days and titrated at different effector:target ratios for killing (4 hrs at 37° C.) of $^{51}$Cr-labeled EL4 tumor target cells.

When human MLC was used, each group of triplicate cultures were set up with 1×10$^6$ responder PBL and 5×10$^5$ mitomycin-c treated allogeneic stimulator PBL. Cultures were pooled at 6 days and titrated for lysis of $^{51}$Cr-labeled, 72 hr ConA activated target PBL blasts from the same donor as was used as stimulator in MLC.

Preparation of Murine CD200Fc and CD200$_{tr}$Fc:

Mouse CD200Fc, in which the extracellular domain of CD200 was linked genetically to a murine IgG2a Fc region, was cloned into a BaculoGold vector and expressed in Sf9 insect cells as described elsewhere. The yield of soluble product in the medium was ~1 μg/ml. Material was concentrated on an anti-Fc affinity column with elution using MgCl$_2$. Production of a soluble form of the truncated product (CD200$_{tr}$Fc) followed a similar protocol, using an alternative 5' primer chosen (see above) to amplify from the alternate start site of the truncated molecule, an identical 3' primer (to that used for the CD200Fc molecule), with cloning and ligation directly into the vector containing the CD200Fc cDNA after restriction enzyme digestion to remove the full-length CD200 cDNA. After cloning the new vector construct was sequenced to confirm ligation of CD200$_{tr}$ into the cassette.

Figure 6:
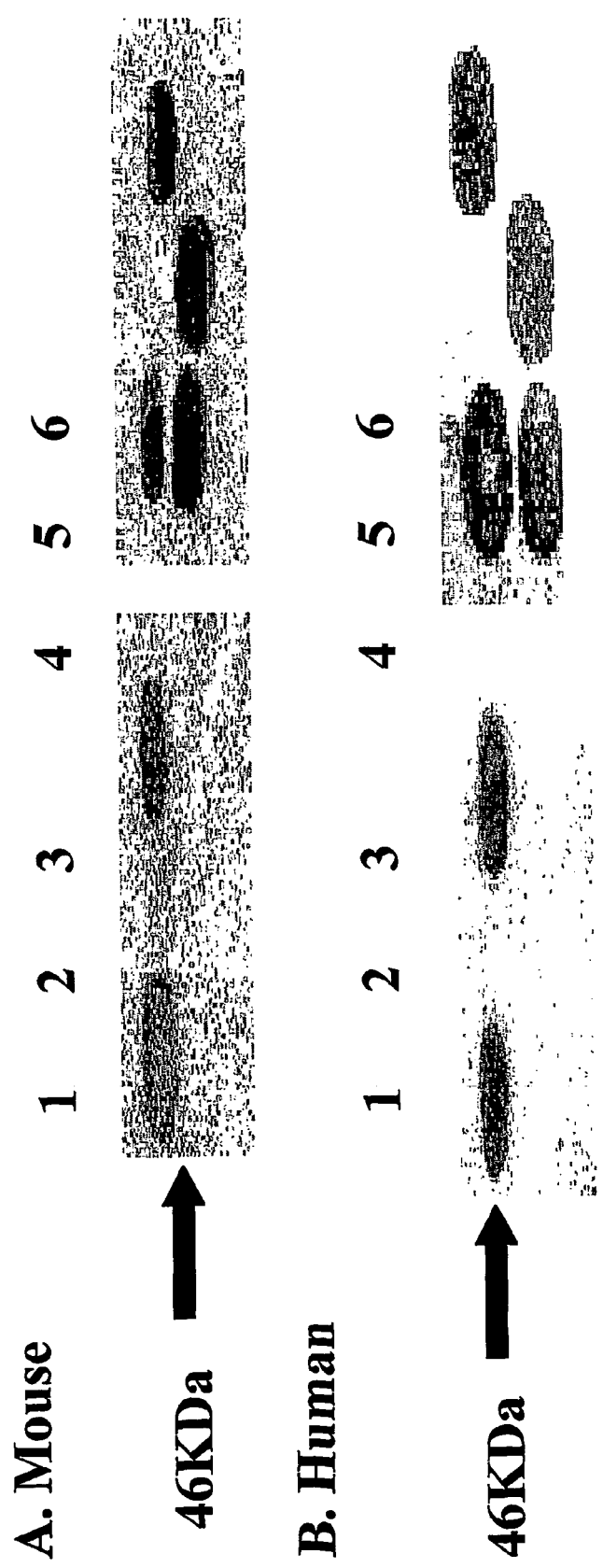
FIG. 6 shows Western gels to show detection of unique Mol. Wt. bands in control CHO cells and CHO cells transduced by human or murine anti-CD200 or anti-$CD200_{tr}$. Fresh tissue extracts were from LPS stimulated human PBL or mouse spleen, or from control CHO cells or CHO transduced with human or murine $CD200/CD200_{tr}$.

Results mAbs to CD200 and CD200$_{tr}$ recognize Distinct Molecules in Western Gels:

LPS stimulated splenic DC were obtained from cells pooled from 3 C57BL/6 mice after overnight incubation with LPS (see Materials and Methods). Human adherent PBL were similarly incubated overnight with LPS. Cells from each sample were extracted in Tris buffer for Western gel analysis, with electrophoresis in 12% SDS-PAGE and transfer to PVDF membranes (Novex Co., San Diego, Calif.). Membranes were screened with anti-CD200 mAb and a putative anti-CD200$_{tr}$, selected by FACS screening as described in the Materials and Methods. Isotype matched rat Ig was used as control. Control lanes also included equivalent protein extracts from control CHO cells and cells transduced to express either full-length human or mouse CD200 or $CD200_{tr}$. Membranes were developed using anti-rat horse radish peroxidase and substrate, with data for a typical blot shown in FIG. 6.

Data in the upper panel, using mouse cell extracts, show that anti-CD200 detected only a 45–48 Kd molecule from the spleen extract, and in CHO cells transduced with full-length CD200-no other band was seen. In contrast, a putative anti-$CD200_{tr}$ antibody, while reacting with an extract of CD200-transfected CHO cells, also detected a smaller band (~35–40 Kd) in both extracts of splenic DC and CHO cells transduced with $CD200_{tr}$. These data are consistent with the predictions of Preston et al, that the immunogenic epitope(s) detected by anti-CD200 mAbs in the full-length CD200 molecule are in the $NH_2$-terminal region of the molecule (and are thus presumably absent in $CD200_{tr}$).

Similar data in the lower panel of this Figure show the specificity of the human anti-CD200 mAb and the anti-human $CD200_{tr}$ mAb, using extracts of LPS stimulated PBL or CHO cells transduced with the respective cDNAs for full-length or truncated human CD200. Once again, an anti-CD200 detected only a single band in DC, while the anti-$CD200_{tr}$ detected 2 bands.

Figure 7:
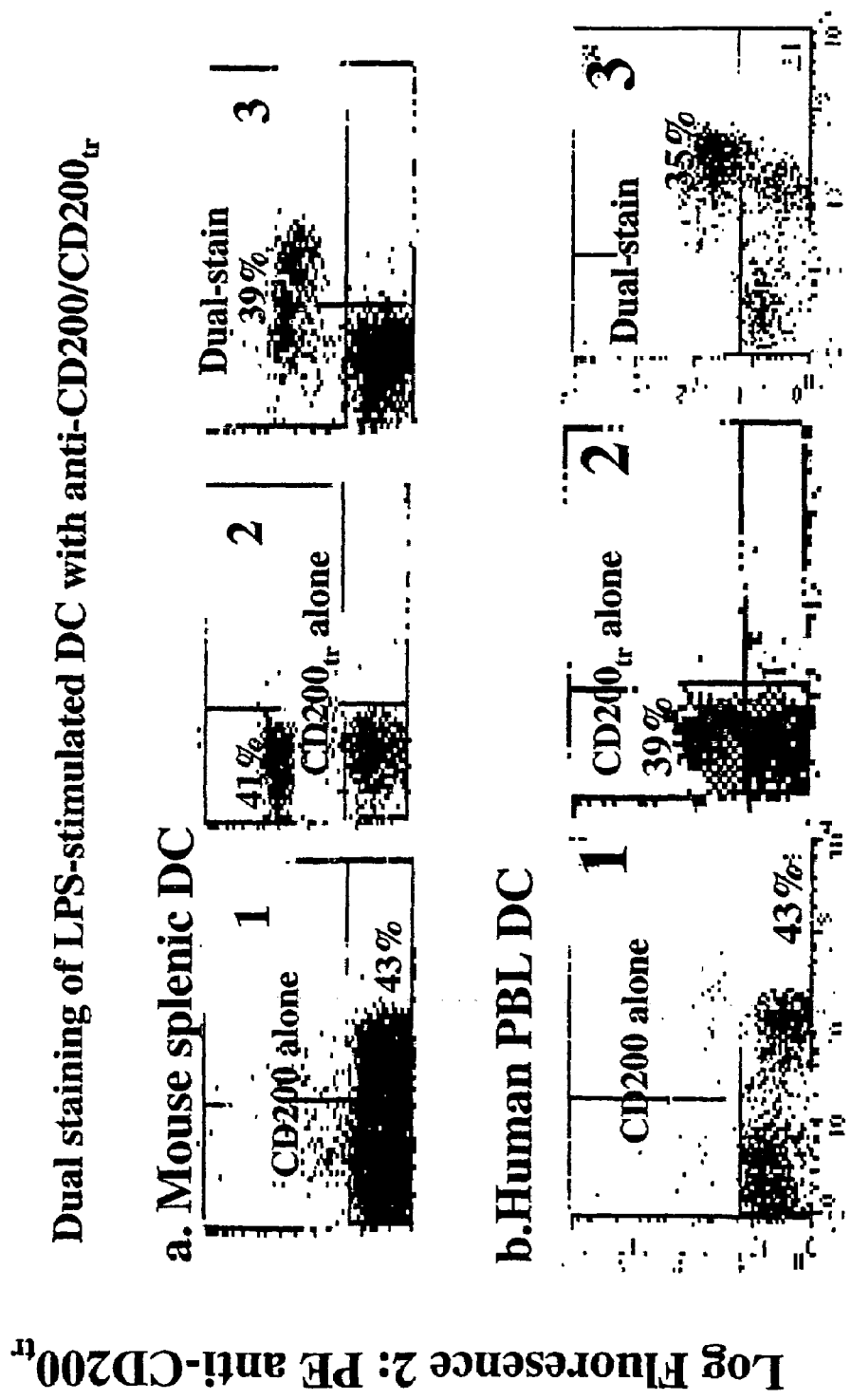
FIG. 7 shows FACS analysis of LPS stimulated mouse splenic DC or human PBL-derived DC shows dual staining of cells with PE-anti-CD200 and FITC-anti-$CD200_{tr}$.

Staining of LPS Stimulated Murine Splenic DC, or Human PBL DC, by Anti-CD200 and Anti-$CD200_{tr}$:

Aliquots of fresh LPS-stimulated murine splenic DC, or human PBL DC, each prepared as above, were stained with homologous PE-anti-CD200 or FITC-$CD200_{tr}$, either alone or sequentially (first with anti-CD200, then anti-$CD200_{tr}$). Data in FIG. 7 (1 of 3 studies) show that $CD200^+$ DC also express $CD200_{tr}$, a result consistent with the two mRNA species found in DC tissue samples.

Figure 8:
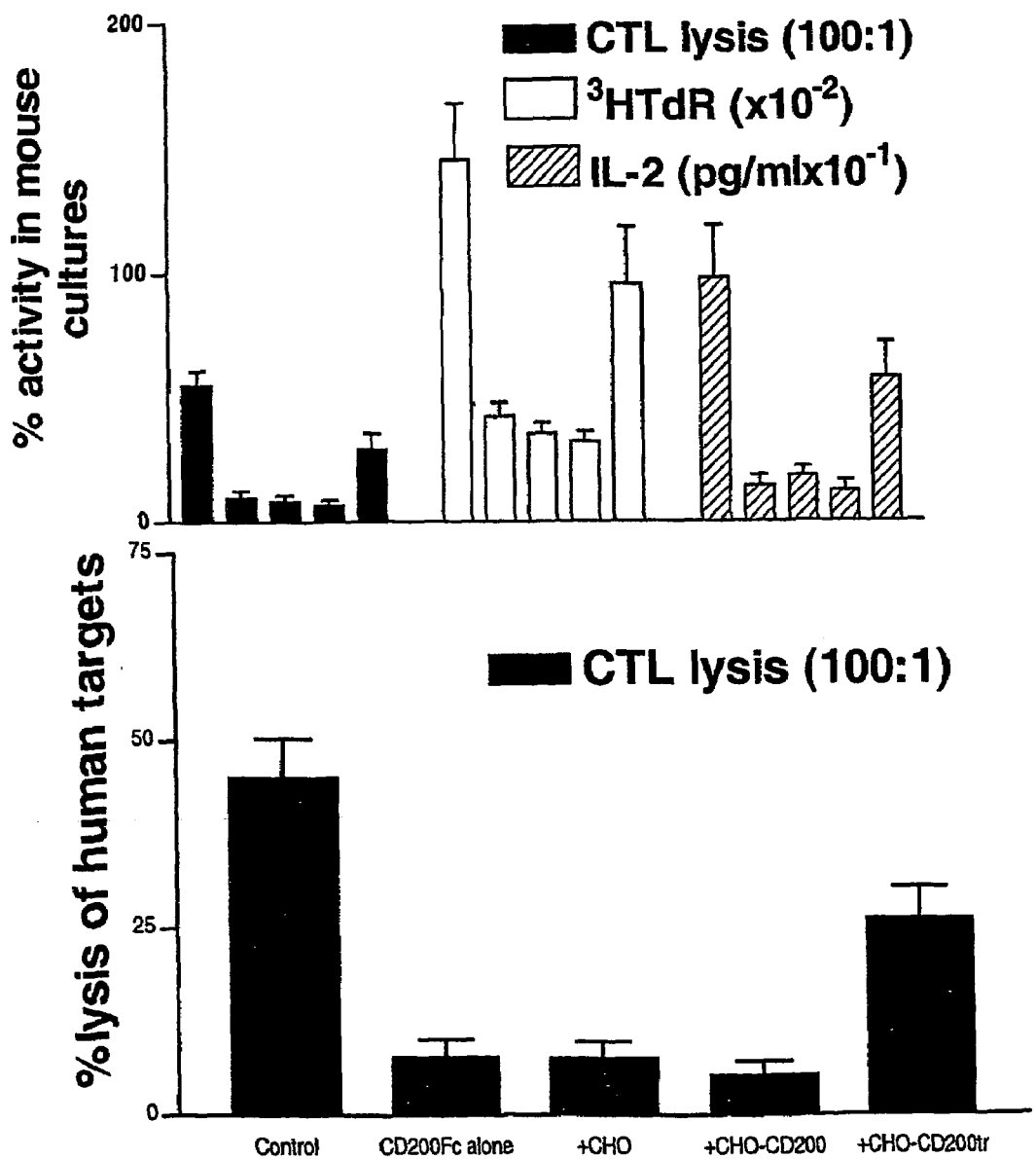
FIG. 8 is a graph showing antagonism of inhibition of MLC reactivity by CD200:Fc in human (panel a) or mouse cultures (panel b) by CHO cells expressing homologous $CD200_{tr}$. Data in panel a are for CTL responses only; in panel b, inhibition of CTL, proliferation ($^3$HTdR) and IL-2 production is shown. In all cases MLC cultures contained $1\times10^6$ responder cells and $5\times10^5$ mitomycin-c treated allogeneic stimulator cells. Experimental cultures contained in addition 100 ng/ml CD200:Fc (either mouse or human), with or without $5\times10^4$ CHO cells (control cells, or transduced with the $CD200/CD200_{tr}$ cDNAs as shown). CTL were assayed at day 6, proliferation at day 3 of culture, and IL-2 production at 48 hrs of culture (see Materials and Methods for more details.

CHO Cells Expressing $CD200_{tr}$ Antagonize Inhibition in MLC Induced by Soluble CD200Fc:

Human or mouse MLC cultures initiated in the presence of 150 ng/ml of the soluble (homologous) immunoadhesin, CD200Fc, show inhibition of CTL induction, proliferation and type-1 cytokine production in vitro. This inhibition is enhanced by inclusion in murine MLC of LPS-stimulated splenic macrophages (Mph) which can be stained by FITC-conjugated CD200Fc (i.e. a $CD200R^+$population). Data shown above indicates that LPS-stimulated DC express both CD200 and $CD200_{tr}$, but these data do not indicate that $CD200_{tr}$ expression has any functional relevance. Accordingly we set up allostimulated MLC cultures for both mouse and human cells, in which we assessed inhibition caused by CD200Fc in the presence or absence of exogenous CHO cells, or CHO transduced with CD200 or $CD200_{tr}$ cDNAs. Data in FIG. 8a/b are typical of results of such studies for human/mouse cells respectively, assessing inhibition of CTL induction (human) or of both CTL, proliferation and IL-2 production (mouse MLC).

These data show clearly that the inhibition produced by soluble CD200Fc is not diminished by inclusion in culture of CHO or CHO cells tranduced with CD200, but is markedly diminished by inclusion of CHO cells transduced with $CD200_{tr}$. Thus $CD200_{tr}$, expressed on the surface of CHO cells, functions as an antagonist of the immunosuppressant function of CD200Fc in these cultures.

Figure 9:
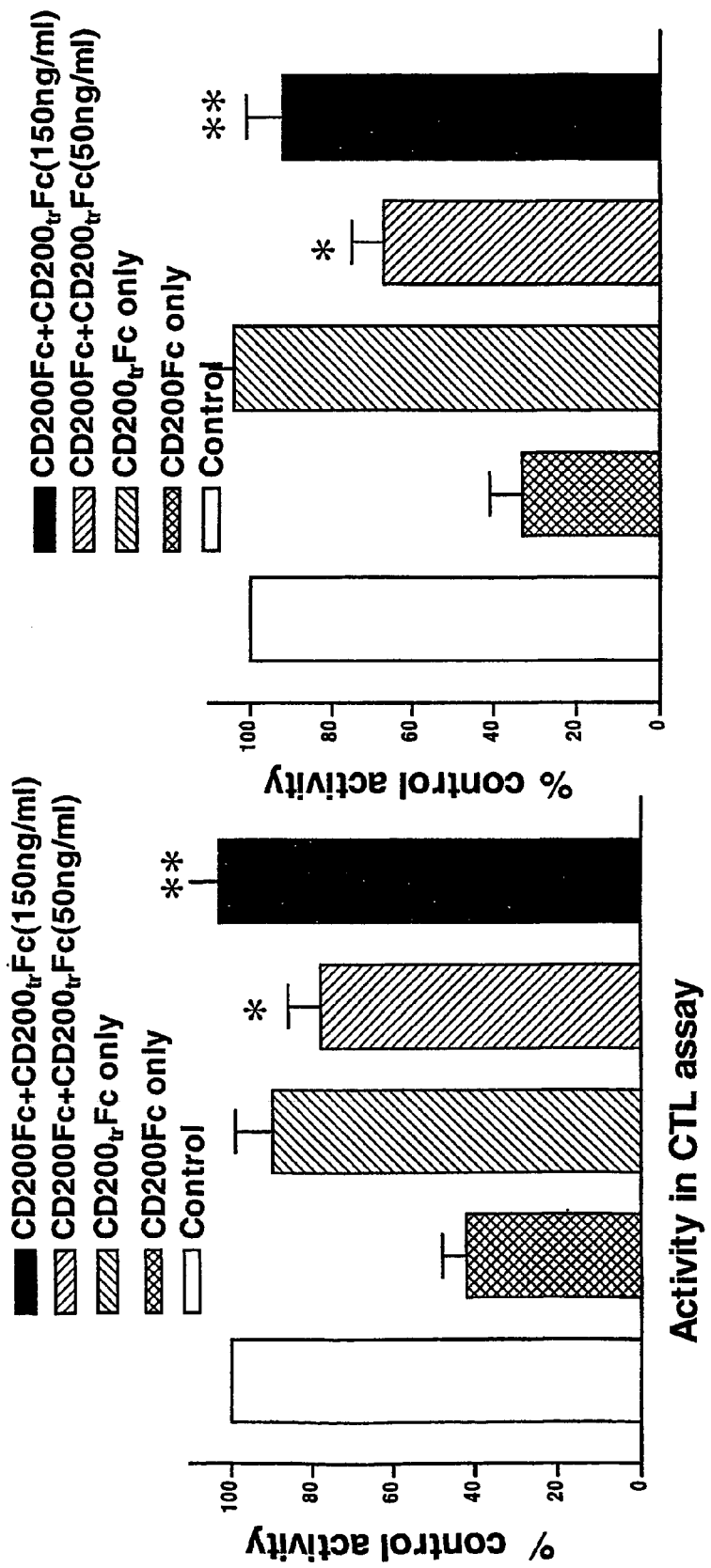
FIG. 9 are bar graphs showing antagonism of suppression of CTL induction and IL-2 production by CD200Fc (150 ng/ml) in MLC cultures by titred amounts (0–150 ng/ml) of $CD200_{tr}$Fc. Cultures contained $5\times10^6$ C3H responder and $2.5\times10^6$ C57BL/6 stimulator spleen cells. IL-2 production was measured (ELISA) in supernatants at 40 hrs of culture. Lysis of $1\times10^4$ EL4 target cells (50:1 effector:target ratio) was estimated in $^{51}$Cr assays at day 5 of culture. Data show mean inhibition ($\pm$SD) of control responses (14$\pm$1.9% lysis; 1050$\pm$190 pg/ml IL-2), in the presence of 150 ng/ml CD200Fc or $CD200_{tr}$Fc alone, or using CD200Fc with additional $CD200_{tr}$Fc. *p<0.05; **, p<0.02, compared with cultures containing CD200Fc alone.

A Soluble Form of $CD200_{tr}$, $CD200_{tr}$Fc, Antagonizes Immunosuppression Mediated by Soluble CD200Fc:

As a final study to examine the potential antagonist properties of $CD200_{tr}$, the effect of adding varying amounts of a soluble form of murine $CD200_{tr}$ ($CD200_{tr}$Fc), prepared in a baculovirus expression system, into MLR cultures initiated in the presence of a fixed amount (150 ng/ml) of the immunosuppressant CD200Fc was examined. Data for this study (one of 3 experiments) are shown in FIG. 9.

These data confirm that the soluble form of $CD200_{tr}$ is a competitive inhibitor for the suppression induced by CD200Fc, whether inhibition is assessed by decreased IL-2 production or lysis of targets by CTL.

DISCUSSION

Unresponsiveness to donor renal allografts following antigen-specific portal vein pre- or peri-transplant immunization is associated with the preferential activation of type-2 rather than type-1 cytokine producing cells. T cell activation depends on signaling via the TCR and the appropriate delivery of costimulatory signals from antigen presenting cells (APC). The inventor has documented a role for another molecule, CD200, in the regulation of alloresponsiveness, and shown that anti-CD200 mAbs reverse increased graft survival following pv immunization, and increase IL-2 production. Based on the lack of any intracellular signaling domains in the CD200 molecule it was earlier hypothesized that CD200 (suppressive) signaling followed engagement of a receptor, CD200R, on a target cell surface, and have recently shown optimal inhibition of graft rejection using a mixture of CD200Fc (a soluble form of CD200) and $CD200R^+$ cells.

RT-PCR studies using RNA extracted from $CD200^+$ expressing lymphohaematopoietic tissue reveals two distinct cDNA bands, one of which corresponds to a splice variant in which exon 2 (encoding part of the leader sequence of CD200) is absent. This is associated with a frameshift in the translated sequence, and an early stop codon. It was thus assumed that no expression from this truncated CD200 ($CD200_{tr}$) occurred (Borriello et al. 1998). However, given the presence of another ATG start codon downstream, which would correct the frameshift following this alternate splicing, the inventor wondered if in fact it was possible to detect translation of this alternate sequence. After deliberate construction of $CD200_{tr}$, and expression in CHO cells, mAbs to both human and murine $CD200_{tr}$ were raised and it was shown that in both species $CD200_{tr}$ expression is seen.

In order to assess the potential function of this truncated form of CD200, $CD200_{tr}$ was expressed in CHO cells (as a surface molecule), and in soluble form linked to a murine IgG2a Fc region ($CD200_{tr}$Fc). Mouse or human MLC cultures were then initiated in the presence of CD200Fc, alone or with the addition of non-transduced CHO or CD200 ($CD200_{tr}$)-transduced CHO. Similar cultures were set up with mouse cells using soluble $CD200_{tr}$Fc as an antagonist to CD200Fc. Data shown in FIGS. 8 and 9 document evidence that $CD200_{tr}$, whether expressed on the cell surface or in soluble form, is a natural antagonist of CD200, as demonstrated by assays of lymphocyte function (induction of CTL, production of IL-2).

There are clear differences in tissue expression of CD200/$CD200_{tr}$. As but one example, brain tissue expresses little to none of the splice variant mRNA, encoding $CD200_{tr}$. Since CD200:CD200R interactions are important in immunoregulation, it thus seems likely that regulation of the relative expression levels of CD200/$CD200_{tr}$ in a given tissue adds yet another level of complexity to immunoregulation by CD200:CD200R interaction. The inventor has already confirmed an important role for CD200:CD200R interactions in transplantation (both allo- and xeno-transplantation) and in an animal model of auto immune disease, collagen-induced arthritis. From studies of a CD200 knockout mouse, Hoek et al. (2000) speculated on a role for CD200:CD200R interactions in regulation in cells of the myeloid differentiation pathway, and inflammatory processes within the central nervous system. Given recent data (Gorczynski and Marsden-unpublished) for a heterogeneity in the CD200R family, with multiple isoforms showing restricted tissue expression, the overall regulation of inflammation and/or immune process by this molecular system will have a crucial importance in many clinical diseases.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

Gorczynski R M, Chen Z, Fu X M, Zeng H., 1998. Increased expression of the novel molecule Ox-2 is involved in prolongation of murine renal allograft survival. Transplantation 1998; 65: 1106.

Gorczynski R M, Cohen Z, Fu X M, Lei J., 1999a. Anti-rat OX-2 blocks increased small intestinal transplant survival after portal vein immunization. Transpl Proc 1999; 31: 577.

Gorczynski R M, Cattral M S, Chen Z G, et al., 1999b. An immunoadhesin incorporating the molecule OX-2 is a potent immunosuppressant that prolongs allo- and xenograft survival. J Immunol 1999; 163: 1654.

Gorczynski R M, Yu K, Clark D., 2000. Receptor engagement on cells expressing a ligand for the tolerance-inducing molecule OX2 induces an immunoregulatory population that inhibits alloreactivity in vitro and in vivo. J Immunol 2000; 165: 4854.

Borriello F, Tizard R, Rue E, Reeves R. Characterization and localization of Mox2, the gene encoding the murine homolog of the rat MRC OX-2 membrane glycoprotein. Mammalian Genome 1998; 9: 114.

Hoek R M, Ruuls S R, Murphy C A., et al. Down-regulation of the macrophage lineage through interaction with OX2 (CD200). Science 2000; 290: 1768.

I claim:

1. An isolated truncated CD200 (CD200$_{tr}$) protein, wherein said CD200$_{tr}$ protein is encoded by a nucleic acid sequence comprising the nucleic acid sequence set forth in SEQ ID NO: 2 or SEQ ID NO: 4 wherein T can also be U.

2. The isolated CD200$_{tr}$ protein according to claim 1 wherein said CD200$_{tr}$ protein is encoded by the nucleic acid sequence comprising SEQ ID NO:2.

3. The isolated CD200$_{tr}$ protein according to claim 1 wherein said CD200tr protein is encoded by the nucleic acid sequence comprising SEQ ID NO: 4.

4. An isolated truncated CD200 (CD200$_{tr}$) protein comprising the amino acid sequence set forth in SEQ ID NO: 6 or SEQ ID NO: 8.

5. The isolated CD200$_{tr}$ protein according to claim 4 comprising the amino acid sequence set forth in SEQ ID 6.

6. The isolated CD200$_{tr}$ protein according to claim 4 comprising the amino acid sequence set forth in SEQ ID NO: 8.

* * * * *